(12) United States Patent
Vassallo et al.

(10) Patent No.: US 10,226,200 B2
(45) Date of Patent: Mar. 12, 2019

(54) USER INTERFACE ENHANCEMENTS FOR PHYSIOLOGICAL PARAMETER MONITORING PLATFORM DEVICES

(75) Inventors: Gregory P. Vassallo, Camillus, NY (US); Thomas A. Myers, Syracuse, NY (US); Janalee Esler, Portland, OR (US); Michele Marie Donovan, Auburn, NY (US); Eric Michael Andreassen, Syracuse, NY (US); Michael D. Garrant, Marcellus, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1233 days.

(21) Appl. No.: 13/440,860

(22) Filed: Apr. 5, 2012

(65) Prior Publication Data

US 2013/0267861 A1 Oct. 10, 2013

(51) Int. Cl.
*G16H 10/00* (2018.01)
*A61B 5/08* (2006.01)
(Continued)

(52) U.S. Cl.
CPC .......... *A61B 5/0816* (2013.01); *G06F 19/00* (2013.01); *G16H 40/63* (2018.01);
(Continued)

(58) Field of Classification Search
CPC ...... G06Q 50/22; G06Q 50/24; G06F 19/322; G06F 19/323–19/327; G06F 19/00;
(Continued)

(56) References Cited

U.S. PATENT DOCUMENTS

| 5,140,519 A | 8/1992 | Friesdorf et al. |
|---|---|---|
| D366,460 S | 1/1996 | Jorgenson |

(Continued)

FOREIGN PATENT DOCUMENTS

| CN | 1356783 A | 7/2002 |
|---|---|---|
| CN | 1649538 A | 8/2005 |

(Continued)

OTHER PUBLICATIONS

Colin Prodigy Press-Mate Prodigy II® Portable Vital Signs Monitors, DRE, Copyright 2009, accessed at: http://www.dremed.com/catalog/product_info.php/products_id/1181; 5 pages.

(Continued)

*Primary Examiner* — Jason S Tiedeman
(74) *Attorney, Agent, or Firm* — Merchant & Gould P.C.

(57) ABSTRACT

A method for configuring a presentation of physiological data for a patient includes identifying one or more physiological sensor modules that are connected in a physiological parameter monitoring device. After the physiological sensor modules are identified, the physiological parameter monitoring device is configured so that display areas are allocated on a display screen of the physiological parameter monitoring device for displaying physiological data for the patient. A separate display area is allocated for each identified physiological module. After one or more physiological sensor modules are detected as being connected, the physiological parameter monitoring device is automatically configured to include one or more additional display areas on the display screen for displaying physiological data for the patient. A separate additional display area is allocated for each of the additional physiological sensor modules that is connected.

8 Claims, 16 Drawing Sheets

(51) Int. Cl.
*G16H 40/63* (2018.01)
*G06F 19/00* (2018.01)
*A61B 5/0205* (2006.01)
*A61B 5/083* (2006.01)
*G16H 10/60* (2018.01)

(52) U.S. Cl.
CPC ......... *A61B 5/02055* (2013.01); *A61B 5/0836* (2013.01); *A61B 2560/0443* (2013.01); *G16H 10/60* (2018.01)

(58) Field of Classification Search
CPC .......... G06F 19/30; G06F 19/32; G06F 19/34; G06F 19/36; G16H 10/00; G16H 10/60; G16H 15/00; G16H 40/00; G16H 40/60; G16H 40/63; G16H 40/67; A61B 5/0816; A61B 5/02055; A61B 5/0836; A61B 2560/0443
USPC .......................................... 705/2, 3; 600/301
See application file for complete search history.

(56) References Cited

U.S. PATENT DOCUMENTS

| | | |
|---|---|---|
| 5,701,894 A | 12/1997 | Cherry et al. |
| 5,749,907 A * | 5/1998 | Mann ................. A61N 1/37 607/27 |
| 5,902,234 A * | 5/1999 | Webb .................. A61B 5/0002 600/300 |
| D427,574 S | 7/2000 | Sawada et al. |
| 6,219,046 B1 | 4/2001 | Thomas et al. |
| D454,139 S | 3/2002 | Feldcamp |
| 6,364,834 B1 | 4/2002 | Reuss et al. |
| 6,398,727 B1 | 6/2002 | Bui |
| 6,416,471 B1 | 7/2002 | Kumar et al. |
| 6,469,717 B1 | 10/2002 | Wineke et al. |
| D465,226 S | 11/2002 | Friedman |
| D468,322 S | 1/2003 | Walker et al. |
| 6,535,714 B2 | 3/2003 | Melker |
| 6,658,276 B2 | 12/2003 | Kiani et al. |
| 6,675,031 B1 | 1/2004 | Porges et al. |
| 6,707,476 B1 | 3/2004 | Hochstedler |
| 6,783,573 B2 | 8/2004 | Richardson |
| 6,828,910 B2 | 12/2004 | VanRyzin et al. |
| D510,582 S | 10/2005 | Hoang |
| D523,440 S | 6/2006 | Hernandez et al. |
| D525,982 S | 8/2006 | Suzuki |
| D527,011 S | 8/2006 | Bixler |
| 7,124,366 B2 | 10/2006 | Foreman et al. |
| 7,134,994 B2 | 11/2006 | Alpert et al. |
| D545,829 S | 7/2007 | Fletcher |
| 7,336,187 B2 | 2/2008 | Hubbard, Jr. et al. |
| 7,360,693 B1 | 4/2008 | Sullivan |
| D575,296 S | 8/2008 | Fairfield |
| 7,409,399 B2 | 8/2008 | Miyamoto |
| D576,634 S | 9/2008 | Clark et al. |
| 7,428,531 B2 | 9/2008 | Barron et al. |
| D579,456 S | 10/2008 | Chen et al. |
| 7,433,827 B2 | 10/2008 | Rosenfeld et al. |
| D586,818 S | 2/2009 | Luck |
| D590,413 S | 4/2009 | Bhat et al. |
| D590,414 S | 4/2009 | Bhat et al. |
| D592,156 S | 5/2009 | Drews et al. |
| D592,675 S | 5/2009 | Bhat et al. |
| 7,565,616 B2 | 7/2009 | Buchmann |
| D598,923 S | 8/2009 | Chen et al. |
| D598,929 S | 8/2009 | Bhat et al. |
| D599,358 S | 9/2009 | Hoefnagels et al. |
| D599,398 S | 9/2009 | Laidlaw et al. |
| D603,416 S | 11/2009 | Poling et al. |
| D607,463 S | 1/2010 | Krieter et al. |
| D608,366 S | 1/2010 | Matas |
| 7,662,106 B2 | 2/2010 | Daniels et al. |
| D612,860 S | 3/2010 | Tarara et al. |
| RE41,236 E | 4/2010 | Seely |
| D614,634 S | 4/2010 | Nilsen |
| 7,765,479 B2 | 7/2010 | Goodwin et al. |
| 7,774,060 B2 | 8/2010 | Westenskow |
| 7,782,302 B2 | 8/2010 | Lee et al. |
| 7,787,946 B2 | 8/2010 | Stahmann et al. |
| 7,810,497 B2 | 10/2010 | Pittman et al. |
| D632,699 S | 2/2011 | Judy et al. |
| 7,895,527 B2 | 2/2011 | Zaleski et al. |
| D635,150 S | 3/2011 | Sykes et al. |
| D637,603 S | 5/2011 | Godgart |
| 7,937,134 B2 | 5/2011 | Uber et al. |
| D640,264 S | 6/2011 | Fujii et al. |
| 7,967,759 B2 | 6/2011 | Couvillon, Jr. |
| D643,043 S | 8/2011 | Loken et al. |
| 8,001,967 B2 | 8/2011 | Wallace et al. |
| 8,020,558 B2 | 9/2011 | Christopher et al. |
| D646,689 S | 10/2011 | Ulliot |
| 8,028,701 B2 | 10/2011 | Al-Ali et al. |
| 8,038,593 B2 | 10/2011 | Friedman et al. |
| 8,046,705 B2 | 10/2011 | Hunleth et al. |
| 8,055,514 B2 | 11/2011 | Elsholz |
| 8,078,983 B2 | 12/2011 | Davis et al. |
| D652,051 S | 1/2012 | Judy et al. |
| D656,153 S | 3/2012 | Imamura et al. |
| D656,157 S | 3/2012 | Khan et al. |
| D656,946 S | 4/2012 | Judy et al. |
| D657,368 S | 4/2012 | Magee et al. |
| D658,196 S | 4/2012 | Wood et al. |
| D658,667 S | 5/2012 | Cho et al. |
| D662,106 S | 6/2012 | Mori et al. |
| D664,971 S | 8/2012 | Lee et al. |
| D664,984 S | 8/2012 | Lee et al. |
| D666,625 S | 9/2012 | Gilmore et al. |
| D667,837 S | 9/2012 | Magee et al. |
| D667,838 S | 9/2012 | Magee et al. |
| D674,401 S | 1/2013 | Trumble et al. |
| D675,218 S | 1/2013 | Arnold et al. |
| D676,863 S | 2/2013 | Ho Kushner et al. |
| D676,864 S | 2/2013 | Velasco et al. |
| D682,292 S | 5/2013 | Mori et al. |
| D688,685 S | 8/2013 | Rhee et al. |
| D689,899 S | 9/2013 | Lee et al. |
| D695,781 S | 12/2013 | Edwards et al. |
| 8,732,604 B2 | 5/2014 | Okamoto et al. |
| D708,210 S | 7/2014 | Capua et al. |
| 8,782,076 B2 | 7/2014 | Rothman et al. |
| D710,879 S | 8/2014 | Elston et al. |
| D711,895 S | 8/2014 | Inose et al. |
| D711,903 S | 8/2014 | Mishra et al. |
| 8,806,366 B2 | 8/2014 | Kim et al. |
| D712,420 S | 9/2014 | Song et al. |
| D714,822 S | 10/2014 | Capua et al. |
| D718,775 S | 12/2014 | Kim et al. |
| D720,772 S | 1/2015 | Cranfill et al. |
| D726,205 S | 4/2015 | Angelides |
| D726,206 S | 4/2015 | Angelides |
| D726,207 S | 4/2015 | Angelides |
| D726,751 S | 4/2015 | Angelides |
| D726,756 S | 4/2015 | Angelides |
| D726,757 S | 4/2015 | Angelides |
| D727,353 S | 4/2015 | Yokota et al. |
| D727,930 S | 4/2015 | Kim et al. |
| D730,376 S | 5/2015 | Ranz et al. |
| D730,927 S | 6/2015 | Lee et al. |
| D732,562 S | 6/2015 | Yan et al. |
| 9,055,870 B2 | 6/2015 | Meador et al. |
| D733,723 S | 7/2015 | Brinda et al. |
| D737,831 S | 9/2015 | Lee et al. |
| 9,131,904 B2 | 9/2015 | Qualey et al. |
| D740,313 S | 10/2015 | Seo et al. |
| 9,173,998 B2 | 11/2015 | Rosinko et al. |
| 9,180,243 B2 | 11/2015 | Michaud |
| 9,223,771 B2 | 12/2015 | Lehrian et al. |
| 9,235,682 B2 | 1/2016 | Vann et al. |
| 9,254,104 B2 | 2/2016 | Judy et al. |
| 9,259,526 B2 | 2/2016 | Barron et al. |
| 9,265,429 B2 | 2/2016 | St. Pierre et al. |
| 9,377,927 B2 | 6/2016 | Sciammarella et al. |

(56) References Cited

U.S. PATENT DOCUMENTS

| | | |
|---|---|---|
| D772,252 S | 11/2016 | Myers et al. |
| 2002/0054141 A1 | 5/2002 | Yen et al. |
| 2002/0078097 A1 | 6/2002 | Chen et al. |
| 2002/0126137 A1 | 9/2002 | Kaestner, Jr. |
| 2002/0177758 A1 | 11/2002 | Schoenberg et al. |
| 2003/0060727 A1 | 3/2003 | Kline |
| 2003/0135087 A1 | 7/2003 | Hickle et al. |
| 2004/0002874 A1 | 1/2004 | Shaffer et al. |
| 2004/0088199 A1 | 5/2004 | Childress et al. |
| 2004/0111045 A1 | 6/2004 | Sullivan et al. |
| 2005/0114374 A1 | 5/2005 | Juszkiewicz et al. |
| 2005/0229110 A1 | 10/2005 | Gegner et al. |
| 2005/0288571 A1 | 12/2005 | Perkins et al. |
| 2006/0149597 A1 | 7/2006 | Powell et al. |
| 2006/0184160 A1* | 8/2006 | Ozaki .................. G16H 10/60 606/1 |
| 2006/0200009 A1 | 9/2006 | Wekell et al. |
| 2006/0228096 A1 | 10/2006 | Hoshino et al. |
| 2006/0229557 A1* | 10/2006 | Fathallah ............... G06F 19/00 604/131 |
| 2006/0247948 A1 | 11/2006 | Ellis et al. |
| 2007/0000494 A1 | 1/2007 | Banner et al. |
| 2007/0067005 A1 | 3/2007 | Schatz et al. |
| 2007/0124240 A1 | 5/2007 | Ireland et al. |
| 2007/0130036 A1 | 6/2007 | Ireland et al. |
| 2007/0150810 A1 | 6/2007 | Katz et al. |
| 2007/0156456 A1 | 7/2007 | Marlatt et al. |
| 2007/0167173 A1 | 7/2007 | Halcrow et al. |
| 2007/0167694 A1 | 7/2007 | Causevic et al. |
| 2007/0174079 A1 | 7/2007 | Kraus |
| 2007/0185390 A1 | 8/2007 | Perkins et al. |
| 2007/0197878 A1* | 8/2007 | Shklarski .......... A61B 5/02055 600/300 |
| 2007/0203744 A1 | 8/2007 | Scholl |
| 2007/0215157 A1 | 9/2007 | Straw |
| 2007/0276261 A1 | 11/2007 | Banet et al. |
| 2008/0012833 A1 | 1/2008 | Beck et al. |
| 2008/0021379 A1 | 1/2008 | Hickle |
| 2008/0055074 A1 | 3/2008 | Gao et al. |
| 2008/0058609 A1 | 3/2008 | Garibaldi |
| 2008/0058614 A1 | 3/2008 | Banet et al. |
| 2008/0072896 A1 | 3/2008 | Setzer et al. |
| 2008/0077026 A1 | 3/2008 | Banet et al. |
| 2008/0086691 A1 | 4/2008 | Hopermann et al. |
| 2008/0103375 A1 | 5/2008 | Kiani |
| 2008/0108884 A1* | 5/2008 | Kiani .................. A61B 5/0002 600/301 |
| 2008/0115081 A1 | 5/2008 | Sankaravadivelu et al. |
| 2008/0155406 A1 | 6/2008 | Naka |
| 2008/0208812 A1 | 8/2008 | Quoc et al. |
| 2008/0229248 A1 | 9/2008 | Fagans et al. |
| 2008/0249377 A1* | 10/2008 | Molducci ............... A61M 1/16 600/301 |
| 2008/0249801 A1 | 10/2008 | Zaleski |
| 2008/0281168 A1* | 11/2008 | Gibson ............... A61B 5/0205 600/301 |
| 2008/0281637 A1 | 11/2008 | Matz |
| 2008/0318529 A1 | 12/2008 | Harb |
| 2009/0005651 A1* | 1/2009 | Ward .................. A61B 5/00 600/300 |
| 2009/0054743 A1* | 2/2009 | Stewart ................ G16H 15/00 600/301 |
| 2009/0054798 A1 | 2/2009 | Varney et al. |
| 2009/0112630 A1 | 4/2009 | Collins, Jr. et al. |
| 2009/0131761 A1 | 5/2009 | Moroney, III et al. |
| 2009/0132588 A1 | 5/2009 | Mahesh et al. |
| 2009/0143652 A1 | 6/2009 | Warburton et al. |
| 2009/0149927 A1 | 6/2009 | Kneuer et al. |
| 2009/0158415 A1 | 6/2009 | Dillon |
| 2009/0240116 A1 | 9/2009 | Bluth |
| 2009/0240193 A1 | 9/2009 | Mensinger et al. |
| 2009/0241958 A1 | 10/2009 | Baker, Jr. |
| 2009/0275805 A1 | 11/2009 | Lane |
| 2009/0275810 A1 | 11/2009 | Ayers et al. |
| 2009/0282340 A1 | 11/2009 | Akaike et al. |
| 2009/0306482 A1 | 12/2009 | Davis et al. |
| 2009/0306488 A1 | 12/2009 | Al-Ali et al. |
| 2009/0312648 A1 | 12/2009 | Chan et al. |
| 2010/0050075 A1 | 2/2010 | Thorson et al. |
| 2010/0069004 A1 | 3/2010 | Bloebaum |
| 2010/0094096 A1 | 4/2010 | Petruzzelli |
| 2010/0097380 A1 | 4/2010 | Daniels |
| 2010/0103189 A1* | 4/2010 | Hao ..................... G06Q 40/06 345/593 |
| 2010/0156654 A1* | 6/2010 | Bullemer .......... G05B 23/0272 340/691.6 |
| 2010/0177100 A1* | 7/2010 | Carnes ................... A61B 5/411 345/440 |
| 2010/0218766 A1 | 9/2010 | Milne |
| 2010/0249540 A1* | 9/2010 | Lisogurski ........... A61B 5/0002 600/301 |
| 2010/0261979 A1* | 10/2010 | Kiani ................... A61B 5/0002 600/301 |
| 2010/0274098 A1 | 10/2010 | Belford et al. |
| 2010/0324380 A1 | 12/2010 | Perkins et al. |
| 2011/0014621 A1 | 1/2011 | Wallaert et al. |
| 2011/0015502 A1 | 1/2011 | Peyser |
| 2011/0071420 A1* | 3/2011 | St. Pierre ........... A61B 5/02055 600/549 |
| 2011/0092838 A1* | 4/2011 | Helfenbein .......... A61B 5/0452 600/516 |
| 2011/0169644 A1 | 7/2011 | Muhsin et al. |
| 2011/0190600 A1* | 8/2011 | McKenna ................ A61B 5/01 600/301 |
| 2011/0205577 A1 | 8/2011 | Mori et al. |
| 2011/0209707 A1 | 9/2011 | Terhark |
| 2011/0227739 A1 | 9/2011 | Gilham et al. |
| 2011/0245630 A1 | 10/2011 | St. Pierre et al. |
| 2011/0246565 A1 | 10/2011 | Irwin et al. |
| 2011/0276338 A1 | 11/2011 | Warner et al. |
| 2011/0290250 A1 | 12/2011 | Olson et al. |
| 2011/0313301 A1 | 12/2011 | Lane et al. |
| 2012/0000470 A1 | 1/2012 | Milne et al. |
| 2012/0016251 A1 | 1/2012 | Zhang et al. |
| 2012/0030610 A1 | 2/2012 | DiPerna et al. |
| 2012/0048090 A1 | 3/2012 | Etter et al. |
| 2012/0094600 A1* | 4/2012 | DelloStritto ......... A61B 5/0015 455/41.2 |
| 2012/0095778 A1* | 4/2012 | Gross .................. G06F 19/3406 705/2 |
| 2012/0096367 A1 | 4/2012 | DelloStritto et al. |
| 2012/0110444 A1 | 5/2012 | Li et al. |
| 2012/0117099 A1 | 5/2012 | Gross |
| 2012/0215075 A1 | 8/2012 | Surace et al. |
| 2012/0296183 A1 | 11/2012 | Kinsley et al. |
| 2013/0151285 A1 | 6/2013 | McLaren et al. |
| 2013/0187780 A1 | 7/2013 | Angelides |
| 2013/0265327 A1 | 10/2013 | Vann et al. |
| 2013/0267792 A1 | 10/2013 | Petersen et al. |
| 2013/0267793 A1 | 10/2013 | Meador et al. |
| 2013/0267861 A1 | 10/2013 | Vassallo et al. |
| 2013/0268283 A1 | 10/2013 | Vann et al. |
| 2013/0293373 A1 | 11/2013 | Gegner et al. |
| 2013/0311926 A1 | 11/2013 | Keegan et al. |
| 2014/0040429 A1 | 2/2014 | Irwin et al. |
| 2014/0059436 A1 | 2/2014 | Swenson et al. |
| 2014/0098209 A1 | 4/2014 | Neff |
| 2014/0108041 A1 | 4/2014 | Bechtel et al. |
| 2014/0135588 A1 | 5/2014 | Al-Ali et al. |
| 2014/0331189 A1 | 11/2014 | Lee et al. |
| 2015/0186023 A1 | 7/2015 | Alisanski et al. |
| 2015/0335296 A1 | 11/2015 | Meador et al. |
| 2016/0085942 A1 | 3/2016 | Vann et al. |
| 2016/0196010 A1 | 7/2016 | Sheha et al. |
| 2016/0196041 A1 | 7/2016 | Lavoie |
| 2016/0196584 A1 | 7/2016 | Franklin et al. |
| 2016/0202866 A1 | 7/2016 | Zambetti et al. |
| 2016/0216868 A1 | 7/2016 | Victor |
| 2016/0217423 A1 | 7/2016 | Magnan et al. |
| 2016/0217599 A1 | 7/2016 | Neels et al. |

(56) References Cited

U.S. PATENT DOCUMENTS

FOREIGN PATENT DOCUMENTS

| | | |
|---|---|---|
| CN | 101069638 A | 11/2007 |
| EP | 0 707 824 | 4/1996 |
| EP | 2 093 683 A2 | 8/2009 |
| GB | 2409951 A | 7/2005 |
| JP | 10-91687 A | 4/1998 |
| JP | 3682617 B2 | 8/2005 |
| JP | 2010-015193 A | 1/2010 |
| WO | 2001026021 A1 | 4/2001 |
| WO | 2001089362 A2 | 5/2001 |
| WO | 2006-076498 A2 | 7/2006 |
| WO | 2010-102069 A2 | 9/2010 |
| WO | 2011-001302 A1 | 1/2011 |

OTHER PUBLICATIONS

Fingertip Pulse Oximeter SPO2 Monitor Oxigen Oximeter; Copyright 1995-2010, accessed at: http://74.125.45.132/search?q=cache:ANfHne9je7gJ:cgi.ebay.com.sg/ws/eBayISAPI.dll%3FViewItem%26item%3D260412542031+"Fingertip+Pulse+Oximeter+SPO2+Monitor+Oxigen+Oximeter"&cd=2&hl=en&ct=clnk&gl=us; 6 pages.

Handheld Pulse Oximeter PM-60A, Contec Medical System Co. Ltd., Jul. 31, 2009; accessed at: http://www.tradeindia.com/selloffer/1858593/Handheld-Pulse-Oximeter-PM-60A.html; 5 pages.

International Search Report and Written Opinion in PCT/US2010/048450 dated Apr. 12, 2011, 9 pages.

mCare 300 Vital Signs Monitor, Spacelabs Medical, Inc., Copyright 2006, 4 pages.

Multiple Vital Signs from One Non-invasive Sensor, Starr™ Life Sciences Corp., Copyright 2009, accessed at: http://www.starrlifesciences.com/mouseox.html; 1 page.

NTIA Handheld Pulse Oximeter, Frontline Systems; Dec. 31, 2009, accessed at: http://www.tradeindia.com/fp385774/NTIA-Handheld-Pulse-Oximeter.html; 3 pages.

Ultraview DM3—Dual Mode Vital Signs Monitor, Spacelabs Healthcare, Copyright 2010, 4 pages.

U.S. Appl. No. 12/751,579, filed Mar. 31, 2010.
U.S. Appl. No. 12/751,602, filed Mar. 31, 2010.
U.S. Appl. No. 61/243,872, filed Sep. 18, 2009.
U.S. Appl. No. 29/353,090, filed Dec. 31, 2009.

International Search Report & Written Opinion in PCT/US2013/031342 dated Jun. 24, 2013, 12 pages.

O'Donoughue, N. et al., Design and Implementation of a Framework for Monitoring Patients in Hospitals Using Wireless Sensors in Ad Hoc Configuration, Engineering in Medicine and Biology Society, 2006. EMBS '06. 28th Annual International Conference of the IEEE, vol., No., Aug. 30, 2006-Sep. 3, 2006, pp. 6449-6452.

Nag, S. et al., Wireless E-Jacket for Multiparameter Biophysical Monitoring and Telemedicine Applications, Medical Devices and Biosensors, 2006. 3rd IEEE/EMBS International Summer School on, vol., No., Sep. 4-6, 2006, pp. 40-44.

Capnography: An Objective Tool for Assessing Respiratory Status, Physio-Control. Capnography: An Objective Tool for Assessing Respiratory Status. Physio-Control, Inc. 2008, pp. 1-8.

Adams, A.P., Breathing System Disconnections, Breathing System Disconnections. Br. J. Anaesth. 1994. vol. 73, No. 1, pp. 46-54.

Al-Qutayri et al.; Framework for Secure Wireless Health monitoring and remote Access System, Inderscience Enterprises Ltd. copyright 2010, 19 pages.

International Search Report and Written Opinion in PCT/US2013/031458 dated Jun. 28, 2013, 10 pages.

International Search Report and Written Opinion in PCT/US2013/031486 dated Jun. 28, 2013, 10 pages.

International Search Report and Written Opinion in PCT/US2013/031582 dated Jun. 28, 2013, 11 pages.

Kozlovszky et al.; Network and Service Management and Diagnostics Solution of a Remote Patient Monitoring System, IEEE copyright 2011, 4 pages.

Lamberti et al.; Ubiquitous Real-Time Monitoring of Critical-Care Patients in Intensive Care Units, IEEE copyright 2003, 4 pages.

Panorama™ Central Station, Surgical Product Guide copyright 2011, 2 pages.

Portable Patient Monitors, Welch Allyn, Copyright 2005-2006 MedDirect, Copyright 2005-2006, accessed at: http://www.meddirect.co.nz/Product.aspx?ProductId=3476;1 page.

Station—Dictionary.com, [online], retrieved on Sep. 2, 2014, Retrived from, <URL: http://dictionary.reference.com/browse/station>, 4 pages.

U.S. Appl. No. 29/417,592, filed Apr. 5, 2012.
U.S. Appl. No. 29/417,611, filed Apr. 5, 2012.

Zhao et al.; A Portable, Low-Cost, Batter-Powered Wireless Monitoring System for Obtaining Varying Physiologic Parameters from Multiple Subjects, IEEE copyright 2006, 4 pages.

Extended European Search Report for PCT/US2010/048450, Nov. 18, 2014, 7 pages.

* cited by examiner

800

| 802 | 6:00 | 7:00 | 8:00 | 8:11+ 806 | 9:00 | 10:00 | 11:00 | 12:00 | 13:00 | 14:00 |
|---|---|---|---|---|---|---|---|---|---|---|
| IPI | ## | ## | ## | ## | ## | ## | ## | ## | ## | ## |
| etCO2 | ## | ## | ## | ## | ## | ## | ## | ## | ## | ## |
| RR | ## | ## | ## | ## | ## | ## | ## | ## | ## | ## |
| SpO2 | ## | ## | ## | ## | ## | ## | ## | ## | ## | ## |
| NIBP | | | | | | | | | | |
| Temp | | | | | | | | | | |

1 hour

Fixed position on table for zoom with alarmed interval column

| 804 | 8:08 | 8:09 | 8:10 | 8:11 | 8:12 | 8:13 | 8:14 | 8:15 | 8:16 | 8:17 |
|---|---|---|---|---|---|---|---|---|---|---|
| IPI | ## | ## | ## | ## | ## | ## | ## | ## | ## | ## |
| etCO2 | ## | ## | ## | ## | ## | ## | ## | ## | ## | ## |
| RR | ## | ## | ## | ## | ## | ## | ## | ## | ## | ## |
| SpO2 | ## | ## | ## | ## | ## | ## | ## | ## | ## | ## |
| NIBP | | | | | | | | | | |
| Temp | | | | | | | | | | |

1 minute

FIG. 8

USER INTERFACE ENHANCEMENTS FOR PHYSIOLOGICAL PARAMETER MONITORING PLATFORM DEVICES

RELATED APPLICATION

The present application is related to U.S. patent application Ser. No. 12/751,579 filed on Mar. 31, 2010, the entirety of which is hereby incorporated by reference.

BACKGROUND

Health care practitioners, such as nurses and physicians, use various types of health-care equipment to assist with the task of providing health care to a patient, also referred to herein as a health-care recipient. Some health-care equipment, referred to as single function equipment, is designed to perform a particular function, such as temperature measurement. Some health-care equipment, referred to as multi-function equipment, is designed to implement the performance of more than one function, such as temperature measurement and blood pressure measurement.

Physiological parameter monitoring platform devices are multi-function equipment that monitor physiologic data from one or more patients. Physiological parameter monitoring platform devices typically provide a user interface to display physiological data corresponding to particular functions. User interfaces for some physiological parameter monitoring platform devices often allocate space for display of particular functions whether the particular functions are being monitored or not.

SUMMARY

One aspect is a method for configuring a presentation of physiological data for a patient. One or more physiological sensor modules are identified that are connected in a physiological parameter monitoring device. After the one or more physiological sensor modules are identified, the physiological parameter monitoring device is configured so that one or more display areas are allocated on a display screen of the physiological parameter monitoring device for displaying physiological data for the patient. A separate display area is allocated for each identified physiological module. One or more additional physiological sensor modules are detected that are connected in the physiological parameter monitoring device. After the one or more physiological sensor modules are detected as being connected, the physiological parameter monitoring device is automatically configured to include one or more additional display areas on the display screen for displaying physiological data for the patient. A separate additional display area is allocated for each of the additional physiological sensor modules that is connected.

Another aspect is a method for reconfiguring a physiological parameter monitoring device from a first workflow to a second workflow. On the physiological parameter monitoring device, physiological data is obtained from a patient according to the first workflow. A determination is made that a first physiological sensor device is being used with the physiological parameter monitoring device. As a result of determining that the first physiological sensor device is being used with the physiological parameter monitoring device, the physiological parameter monitoring device is reconfigured to the second workflow. Physiological data is obtained from the patient according to the second workflow.

Yet another aspect is a method for viewing physiological data on a display screen of a physiological parameter monitoring device. On the display screen, first physiological data is displayed for a patient at first time intervals. The first physiological data is displayed in tabular form. An alarm is received at the physiological parameter monitoring device. The alarm occurs at a time within one of the first time intervals. As a result of displaying the alarm, a column of physiological data is displayed corresponding to the time at which the alarm occurred. The column of physiological data corresponding to the time at which the alarm occurred is selected. As a result of selecting the column of physiological data corresponding to the time at which the alarm occurred, second physiological data is displayed for the patient at second time intervals. The second time intervals are shorter than the first time intervals.

Yet another aspect is a method for generating a warning at a physiological parameter monitoring device. A determination is made that a respiration sensor device is attached to the physiological parameter monitoring device. When it is determined that the respiration sensor device is attached to the physiological parameter monitoring device, a warning message is displayed to a user of the physiological parameter monitoring device.

BRIEF DESCRIPTION OF THE DRAWINGS

The present disclosure can be better understood with reference to the claims and drawings described below. The drawings are not necessarily to scale, and the emphasis is instead generally being placed upon illustrating the principles of the invention. Within the drawings, like reference numbers are used to indicate like parts throughout the various views. Differences between like parts may cause those like parts to be each indicated by different reference numbers. Unlike parts are indicated by different reference numbers.

FIG. 8 illustrates an example review zoom feature of the user interface for the physiological parameter monitoring platform device of FIG. 2A.

DETAILED DESCRIPTION

Figure 1:
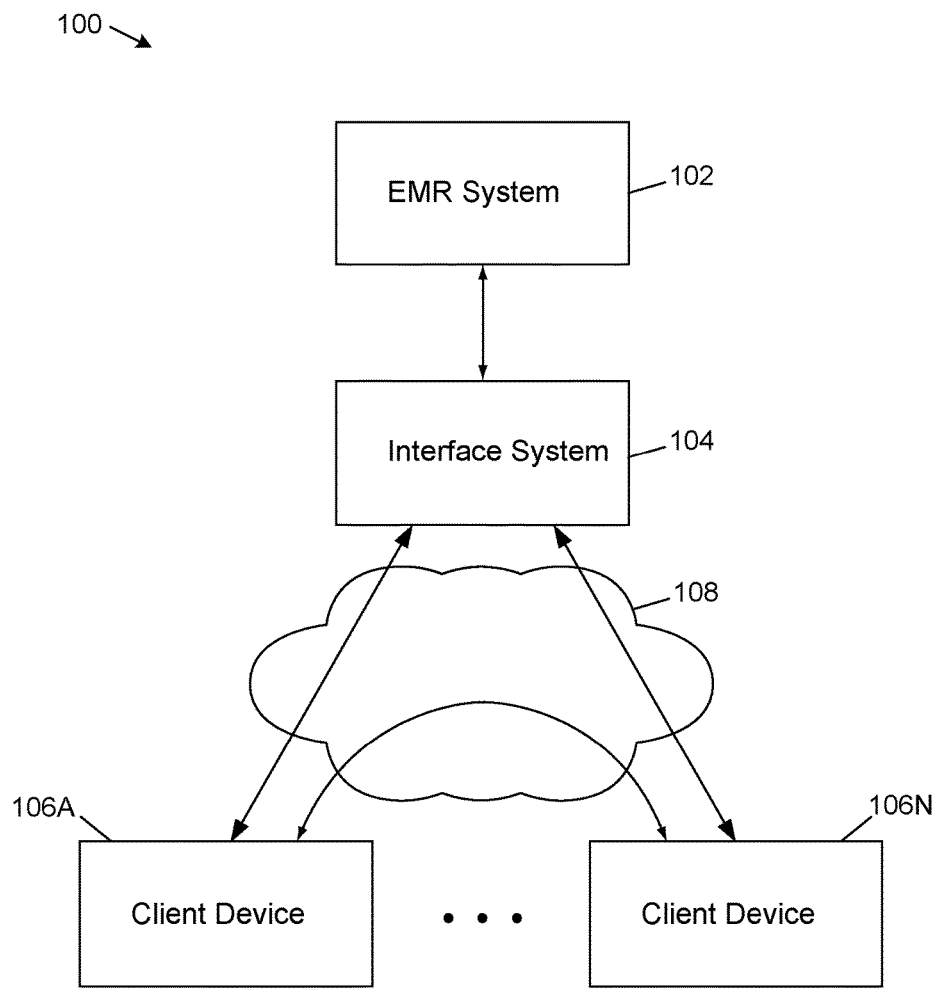
FIG. 1 is a block diagram illustrating an example system for collecting measurements of physiological parameters of patients.

Embodiments of the present disclosure are directed to a physiological parameter monitoring platform (PMP) device having a user interface configured to operate within and transition between each of a continuous workflow, a monitoring workflow and a non-monitoring workflow. Embodiments of the present disclosure are directed to technological problems associated with display of patient-related data, such as physiological parameters, on physiological parameter monitoring devices. Example technological problems associated with physiological parameter monitoring device displays include efficiently managing screen real estate to provide relevant patient-related data for caregiver viewing.

In some examples described herein, the PMP device is a portable device. In other examples, the PMP device is a non-portable device, such as a computing device like a workstation. Many configurations are possible.

In the following detailed description, references are made to the accompanying drawings that form a part hereof, and in which are shown by way of illustrations specific embodiments or examples. These embodiments may be combined, other embodiments may be utilized, and structural changes may be made without departing from the spirit or scope of the present invention. The following detailed description is therefore not to be taken in a limiting sense and the scope of the present invention is defined by the appended claims and their equivalents.

Referring now to the drawings, in which like numerals refer to like elements through the several figures, aspects of the present invention and an exemplary computing operating environment will be described.

FIG. 1 is a block diagram illustrating an example system 100 for collecting measurements of physiological parameters of patients. As illustrated in the example of FIG. 1, the system 100 comprises an Electronic Medical Records (EMR) system 102, an interface system 104, a set of client devices 106A-106N (collectively, "client devices 106"), and a network 108.

The network 108 is an electronic communication network that facilitates communication between the client devices 106 and the between the client devices 106 and the interface system 104.

An electronic communication network is a set of computing devices and links between the computing devices. The computing devices in the network use the links to enable communication among the computing devices in the network. The network 108 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices. In various embodiments, the network 108 includes various types of links. For example, the network 108 can include wired and/or wireless links.

Furthermore, in various embodiments, the network 108 is implemented at various scales. For example, the network 108 can be implemented as one or more local area networks (LANs), metropolitan area networks, subnets, wide area networks (such as the Internet), or can be implemented at another scale.

The EMR system 102 is a computing system that allows storage, retrieval, and manipulation of electronic medical records. As used herein, a computing system is a system of one or more computing devices. A computing device is a physical, tangible device that processes data. Example types of computing devices include personal computers, stand-alone server computers, blade server computers, mainframe computers, handheld computers, smart phones, special purpose computing devices, and other types of devices that process data.

Each client device in the set of client devices 106 is a computing device. The client devices 106 can provide various types of functionality. For example, the set of client devices 106 can include one or more PMP devices (such as the PMP device 200). In addition, the set of client devices 106 can include one or more desktop, laptop, or wall-mounted devices. Such wall-mounted devices can have similar functionality to the PMP device 200 but are stationary instead of portable.

In addition, the set of client devices 106 can include one or more PMP devices. Such monitor devices can display representations of physiological parameters. A monitor device could, for example, be used by a clinician to monitor the physiological parameters of multiple patients at one time. Such monitor devices are typically not wall mounted.

The client devices 106 can communicate with each other through the network 108. In various embodiments, the client devices 106 can communicate various types of data with each other through the network 108. For example, in embodiments where the set of client devices 106 includes a set of PMP devices and a monitor device, each of the PMP devices can send data representing measurements of physiological parameters of patients to the monitor device. In this way, the monitor device can display representations of physiological parameters to a clinician.

The interface system 104 is a computing system that acts as an interface between the EMR system 102 and the client devices 106. In some embodiments, the interface system 104 is a CONNEX™ interface system from Welch Allyn of Skaneateles Falls, N.Y., although other interface systems can be used. Different EMR systems have different software interfaces.

For example, the EMR system used by two different hospitals can have two different software interfaces. The interface system 104 provides a single software interface to each of the client devices 106. The client devices 106 send requests to software interface provided by the interface system 104. When the interface system 104 receives a request from one of the client devices 106, the interface system 104 translates the request into a request that works with the software interface provided by the EMR system 102. The interface system 104 then provides the translated request to the software interface provided by the EMR system 102. When the interface system 104 receives a response from the EMR system 102, the interface system 104 translates the response from a format of the EMR system 102 to a system understood by the client devices 106. The interface system 104 then forwards the translated response to an appropriate one of the client devices 106.

The client devices 106 can send various types of data to the interface system 104 for storage in the EMR system 102 and can receive various types of data from the EMR system 102 through the interface system 104. For example, in some embodiments, the client devices 106 can send measurements of physiological parameters to the interface system 104 for storage in the EMR system 102. In another example, a monitor device can retrieve past measurements of physiological parameters of patients from the EMR system 102 through the interface system 104.

Figure 2A:
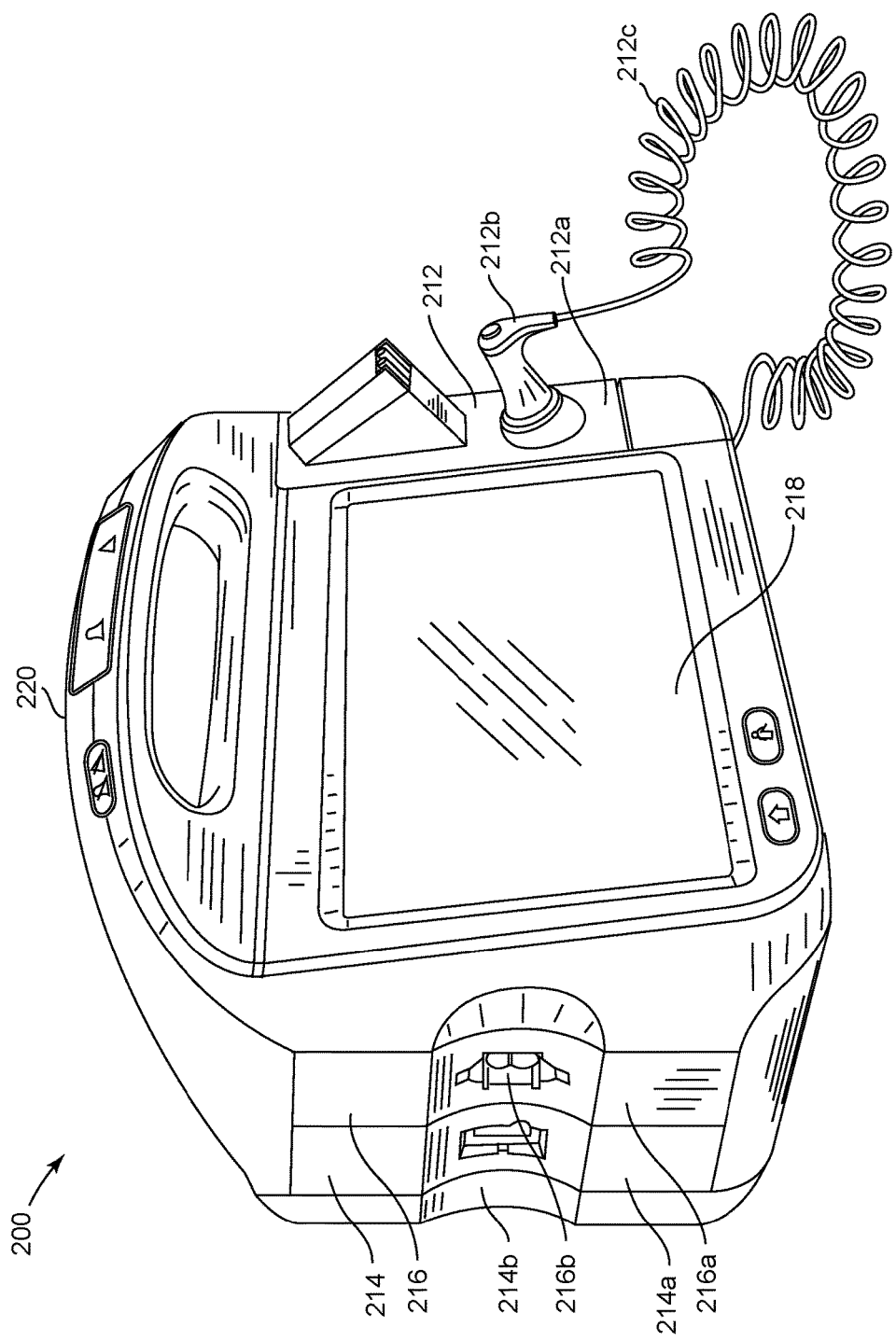
FIG. 2A illustrates a view of an example physiological parameter monitoring platform device.

FIG. 2A illustrates a view of an example PMP device 200. The PMP device 200 is portable. The PMP device 200 includes multiple health care equipment (HCE) modules. Each of the HCE modules is configured to measure one or more physiological parameters of a health-care recipient, also referred to herein as a patient.

A temperature measurement module 212 is accessible from the front side of the PMP device 200. A SpO2 module 214 and a non-invasive blood pressure (NIBP) module 216 are accessible from a left hand side of the PMP device 200. An upper handle portion 220 enables the PMP device 200 to be carried by hand.

A front side of the PMP device 200 includes a display screen 218 and an outer surface of the temperature measurement module 212. The temperature measurement module 212 is designed to measure the body temperature of a patient. As used in this document, a "module" is a combination of a physical module structure which typically resides within the PMP device 200 and optional peripheral components (not shown) that typically attach to and reside outside of the PMP device 200.

The temperature measurement module 212 includes a front panel 212*a*. The front panel 212*a* has an outer surface that is accessible from the front side of the PMP device 200. The front panel 212*a* provides access to a wall (not shown) storing a removable probe (not shown), also referred to as a temperature probe, that is attached to a probe handle 212*b*. The probe and its attached probe handle 212*b* are tethered to the temperature measurement module 212 via an insulated conductor 212*c*. The probe is designed to make physical contact with a patient in order to sense a body temperature of the patient.

A left hand side of the PMP device 200 includes an outer surface of the SpO2 module 214 and an outer surface of the NIBP module 216. The SpO2 module 214 is a HCE module designed to measure oxygen content within the blood of a patient. The NIBP module 216 is a HCE module designed to measure blood pressure of a patient.

As shown, the SpO2 module 214 includes a front panel 214*a*. The front panel 214*a* includes an outer surface that is accessible from the left side of the PMP device 200. The front panel 214*a* includes a connector 214*b* that enables a connection between one or more peripheral SpO2 components (not shown) and a portion of the SpO2 module 214 residing inside the PMP device 200. The peripheral SpO2 components reside external to the PMP device 200. The peripheral SpO2 components are configured to interoperate with the SpO2 module 214 when connected to the SpO2 module 214 via the connector 214*b*. In some embodiments, the peripheral SpO2 components include a clip that attaches to an appendage of a patient, such as a finger. The clip is designed to detect and measure a pulse and an oxygen content of blood flowing within the patient.

As shown, the NIBP module 216 includes a front panel 216*a* having an outer surface that is accessible from the left side of the PMP device 200. The front panel 216*a* includes a connector 216*b* that enables a connection between one or more peripheral NIBP components (not shown) and a portion of the NIBP module 216 residing inside the PMP device 200. The peripheral NIBP components reside external to the PMP device 200. The peripheral NIBP components are configured to interoperate with the NIBP module 216 when connected to the NIBP module 216 via the connector 216*b*. In some embodiments, the peripheral NIBP components include an inflatable cuff that attaches to an appendage of a patient, such as an upper arm of the patient. The inflatable cuff is designed to measure the systolic and diastolic blood pressure of the patient, the mean arterial pressure (MAP) of the patient, and the pulse rate of blood flowing within the patient.

The PMP device 200 is able to operate within one or more workflows. A workflow is a series of one or more tasks that a user of the PMP device 200 performs. When the PMP device 200 operates within a workflow, the PMP device 200 provides functionality suitable for assisting the user in performing the workflow. When the PMP device 200 operates within different workflows, the PMP device 200 provides different functionality.

When the PMP device 200 is manufactured, the PMP device 200 is configured to be able to operate within one or more workflows. After the PMP device 200 is manufactured, the PMP device 200 can be reconfigured to operate within one or more additional workflows. In this way, a user can adapt the PMP device 200 for use in different workflows as needed.

In various embodiments, the PMP device 200 operates within various workflows. For example, in some embodiments, the PMP device 200 can operate within a monitoring workflow or a non-monitoring workflow. Example types of non-monitoring workflows include, but are not limited to, a spot check workflow and a triage workflow.

In example embodiments, the names for the workflows can be defined by the user. For example, the user can rename a "triage workflow" as "ED 3 North" or any other nomenclature as desired to provide more context to the user.

When the PMP device 200 is operating within the monitoring workflow, the PMP device 200 obtains a series of measurements of one or more physiological parameters of a single monitored patient over a period of time. In addition, the PMP device 200 displays, on the display screen 218, a monitoring workflow home screen. The monitoring workflow home screen contains a representation of a physiological parameter of the monitored patient. The representation is based on at least one measurement in the series of measurements. A representation of a physiological parameter is a visible image conveying information about the physiological parameter.

For example, when the PMP device 200 is operating within the monitoring workflow, the PMP device 200 can obtain a blood pressure measurement of a single patient once every ten minutes for six hours. In this example, the PMP device 200 displays a monitoring workflow home screen that contains a representation of the patient's blood pressure based on a most recent one of the temperature measurements. In this way, a user of the PMP device 200 can monitor the status of the patient.

When the PMP device 200 is operating within a non-monitoring workflow, the PMP device 200 obtains a measurement of one or more physiological parameters from each patient in a series of patients. In addition, the PMP device 200 displays a non-monitoring workflow home screen on the display screen 218. The non-monitoring workflow home screen contains a representation of the physiological parameter of a given patient in the series of patients. The representation is based on the measurement of the physiological parameter of the given patient.

In one example, when the PMP device 200 is operating within a spot check workflow, the PMP device 200 obtains blood pressure measurements from a series of previously-identified patients. In this other example, the PMP device 200 displays a spot check workflow home screen containing a blood pressure measurement of a given patient in the series of previously-identified patients. In this way, a user of the PMP device 200 can perform spot checks on the blood pressures of patients who have already been admitted to a hospital.

As used in this document, a patient is a previously identified patient when the PMP device 200 stores information regarding the identity of the patient. In another example, when the PMP device 200 is operating within a triage workflow, the PMP device 200 can obtain a single blood pressure measurement from each patient in a series of unidentified patients as the patients arrive at a hospital. In this example, the PMP device 200 displays a triage workflow home screen containing a representation of the patients' blood pressure based on the single blood pressure measurements of the patients. In this way, a user of the PMP device 200 can perform triage on the series of unidentified patients as they arrive. As used in this document, a patient is an unidentified patient when the PMP device 200 does not store information regarding the identity of the patient.

The monitoring workflow home screen is different than the non-monitoring workflow home screen. Further, as discussed below, the navigation options associated with the different workflows allows for efficient monitoring based on the environment in which the device is used. In various embodiments, the monitoring workflow home screen is different than the non-monitoring workflow home screen in various ways. For example, in some embodiments, the monitoring workflow home screen includes at least one user-selectable control that is not included in the non-monitoring workflow home screen. In other embodiments, a representation of a physiological parameter in the monitoring workflow home screen has a different size than a representation of the same physiological parameter in the non-monitoring workflow home screen.

Figure 2B:
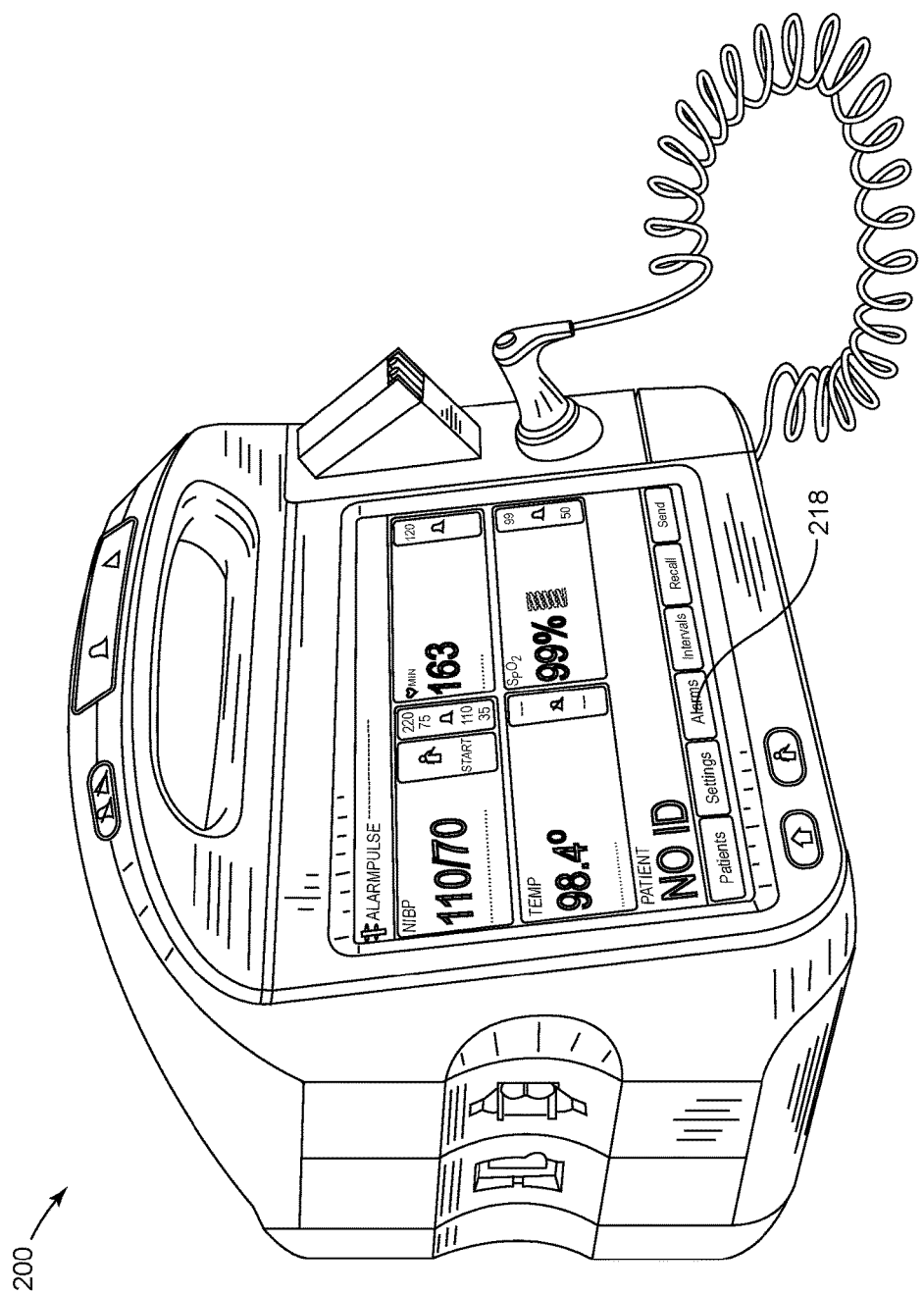
FIG. 2B illustrates an example user interface displayed on a user interface display of the physiological parameter monitoring platform device of FIG. 2A.

FIG. 2B illustrates an example user interface displayed on the display screen 218 of FIG. 2A. The PMP device 200 outputs and displays user interfaces discussed in this document on the display screen 218.

Figure 3:
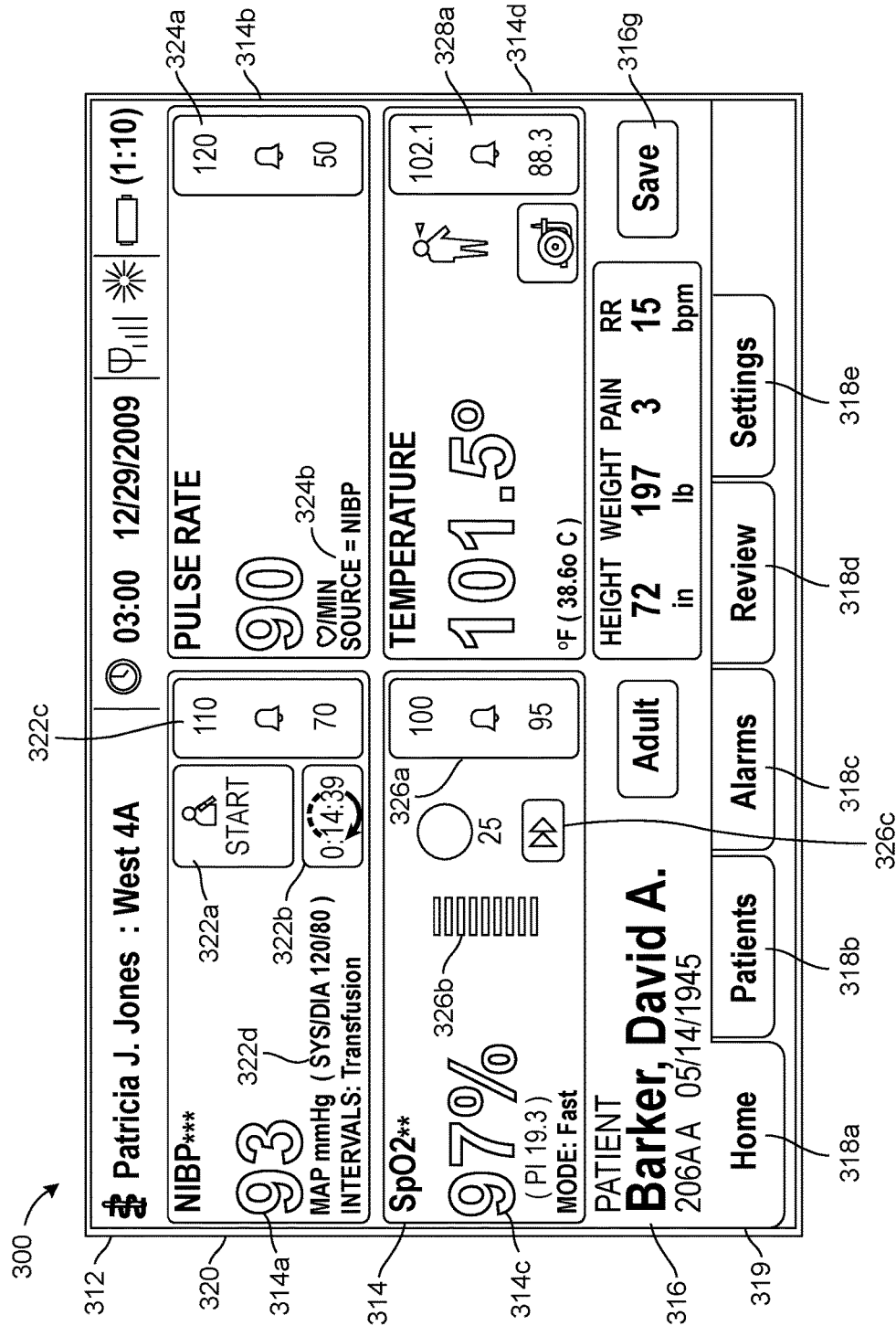
FIG. 3 illustrates another example user interface displayed on a user interface display of the physiological parameter monitoring platform device of FIG. 2A.

FIG. 3 illustrates an example monitoring workflow home screen 300. The PMP device 200 displays the monitoring workflow home screen 300 while the PMP device 200 is operating within a monitoring workflow. The monitoring workflow is designed for obtaining a series of physiological measurements associated with an identified patient over a period of time.

The PMP device 200 is functionally connected to one or more sensors that enable monitoring of at least one physiological parameter that is associated with a patient. Typically, each sensor is physically attached to the patient while the PMP device 200 is operating within the monitoring workflow. These sensors include a temperature probe, a SpO2 clip, and a NIBP blood pressure cuff that are each attachable to the PMP device 200 as described above.

As shown in the example of FIG. 3, the monitoring workflow home screen 300 includes a device status area 312, a navigation area 319, and a content area 320. The content area 320 is divided into a parameter reporting area 314 and a patient attribute area 316.

The device status area 312 contains data regarding a status of the PMP device 200. In the example of FIG. 3, the device status area 312 includes text that identifies a clinician ("Patricia Jones") and a health care facility location ("West 4A"). A current time of day value ("03:00") is located towards the center of the device status area 312. A date value ("Dec. 29, 2009") is located to the right side of the time of day value. A remaining time of a battery ("1:10") value is located at the right side of the device status area 312.

The navigation area 319 includes a home tab 318a, a patients tab 318b, an alarms tab 318c, a review tab 318d, and a settings tab 318e. Collectively, the home tab 318a, the patients tab 318b, the alarms tab 318c, the review tab 318d, and the settings tab 318e are referred to herein as the screen tabs. Selection of screen tabs 318b-318e causes substitution of the monitoring workflow home screen 300 with another screen associated with the screen tabs 318b-318e. For example, the PMP device 200 displays a patient screen when a user selects the patients tab 318b. When the PMP device 200 displays a screen other than the monitoring workflow home screen 300 and a user selects the home tab 318a, the PMP device 200 displays the monitoring workflow home screen 300.

The parameter reporting area 314 includes one or more parameter reporting frames. Each of the parameter reporting frames contains a representation of a different physiological parameter a patient. The representations are based on one or more measurements of the physiological parameters of a monitored patient. In addition, each of the parameter reporting frames contains an alarm reporting area. The alarm reporting areas specify upper alarm limits and lower alarm limits for the physiological parameters. The upper alarm limits and the lower alarm limits define the alarm ranges for the physiological parameters. Alarms associated with the physiological parameters are active when measurements of the physiological parameters are outside the alarm range for the physiological parameters.

In the example of FIG. 3, the parameter reporting area 314 contains a NIBP frame 314a, a pulse rate frame 314b, a SpO2 frame 314c, and a temperature frame 314d. The NIBP frame 314a is located within an upper left portion of the parameter reporting area 314. The pulse rate frame 314b is located within an upper right portion of the parameter reporting area 314. The SpO2 frame 314c is located within a lower left portion of the parameter reporting area 314. The temperature frame 314d is located within a lower right portion of the parameter reporting area 314.

The NIBP frame 314a contains a representation of the blood pressure of the patient. The representation of the blood pressure of the patient is based on one or more measurements of the blood pressure of the patient. In various embodiments, the NIBP frame 314a contains various representations of the blood pressure of the patient. In the example of FIG. 3, the NIBP frame 314a includes enlarged numerical text that represents a MAP in mmHg ("93") of the patient. The NIBP frame 314a also lists a systolic blood pressure value ("120") and a diastolic blood pressure value ("80"), separated from each other via a slash '/' text character, collectively pressure 322d. The systolic blood pressure value is located at the left side of the NIBP frame 314a and the diastolic blood pressure is located to the right side of the systolic blood pressure value.

An NIBP alarm status area 322c is located at the right side of the NIBP frame 314a. The NIBP alarm status area 322c specifies an upper alarm limit and a lower alarm limit for the patient's systolic blood pressure and an upper alarm limit and a lower alarm limit for the patient's diastolic blood pressure. The upper alarm limit and the lower alarm limit for the patient's systolic blood pressure define a systolic blood pressure alarm range. The upper alarm limit and the lower alarm limit for the patient's diastolic blood pressure define a diastolic blood pressure alarm range. An alarm associated with the patient's blood pressure is active when the patient's systolic blood pressure is outside the systolic blood pressure alarm range or when the patient's diastolic blood pressure is outside the diastolic blood pressure alarm range The NIBP frame 314a also contains a NIBP cuff inflation start/stop button 322a. The NIBP cuff inflation stop button 322a is labeled with the text "START." The NIBP frame 314a also contains a NIBP automatic interval timer 322b. The NIBP automatic interval timer 322b is located between the diastolic blood pressure value and the NIBP alarm status area 322c. Selection of the NIBP cuff inflation button 322a starts and ceases inflation of the NIBP cuff and toggles the label of the NIBP cuff inflation button 322a to display the relevant status text (i.e., "START" or "STOP"). As used herein, a user selects a button or control when the user provides input to the PMP device 200 that specifies the control. For example, a user can select a control by pressing the control, by pressing another button while the control is highlighted, or by another means. Selection of the NIBP cuff inflation button 322a (now labeled the "Start" button) restarts inflation of the NIBP cuff and toggles the label of the NIBP cuff inflation stop button 322a to display the ("Stop") text. The NIBP automatic interval timer 322b indicates an amount of time remaining before the next scheduled inflation of the NIBP cuff. Additionally, a user can determine the age of the current NIBP reading on the NIBP frame 314a by subtracting the remaining time on the NIBP automatic interval timer 322b from the original interval duration.

The pulse rate frame 314b contains a representation of the patient's pulse rate. The representation of the patient's pulse rate is based on one or more measurements of the patient's pulse rate. In different embodiments, the pulse rate frame 314b contains different representations of the patient's pulse rate. In the example of FIG. 3, the pulse rate frame 314b includes enlarged numerical text that represents a pulse rate value ("90"). The pulse rate value ("90") is located at the left side of the pulse rate frame 314b. A pulse rate alarm status area 324a is located at the right side of the pulse rate frame 314b. The pulse rate frame 314b also indicates a source of the pulse rate in an extended label field 324b.

The pulse rate alarm status area 324a specifies an upper alarm limit and a lower alarm limit. The upper alarm limit and the lower alarm limit define a pulse rate alarm range. An alarm associated with the patient's pulse rate is active when the patient's pulse rate is outside the pulse rate alarm range.

The SpO2 frame 314c contains a representation of the patient's SpO2 level. The representation of the patient's SpO2 level is based on one or more measurements of the patient's SpO2 level. In different embodiments, the SpO2 frame 314c contains different representations of the patient's SpO2 level. In the example of FIG. 3A, the SpO2 frame 314c includes enlarged numerical text that represents an SpO2 value ("97%"). The SpO2 value ("97%") is located at the left side of the SpO2 frame 314c and is accompanied by a "%" text character on the right side of the SpO2 value. A SpO2 alarm status area 326a is located at the right side of the SpO2 frame 314c. An SpO2 alarm parameter, appearing as a circle adjacent to the text ("25"), indicates a duration of time. The SpO2 alarm status area 326a specifies an upper alarm limit and a lower alarm limit. The upper alarm limit and the lower alarm limit define a SpO2 alarm range. An alarm associated with the patient's SpO2 level is active when the patient's SpO2 level is outside the SpO2 alarm range for the duration of time indicated by the SpO2 alarm parameter 326d. The SpO2 frame 314c also includes a pulse amplitude blip bar 326b which indicates pulse beat and shows the relative pulse amplitude. As the detected pulse becomes stronger, more bars in the pulse amplitude blip bar 326b light up with each pulse. The SpO2 frame 314c also includes an SpO2 response time control button 326c that is configured for a user to control the SpO2 alarm parameter.

The temperature frame 314d contains a representation of the patient's body temperature. The representation of the patient's body temperature is based on one or more measurements of the patient's body temperature. In different embodiments, the temperature frame 314d contains different representations of the patient's body temperature. In the example of FIG. 3, the temperature frame 314d includes enlarged numerical text that represents a temperature value ("101.5"). The temperature value ("101.5") is located at the left side of the temperature frame 314d and is accompanied by a Fahrenheit degree indicating symbol on the right side of the temperature value. A temperature alarm status area 328a is located at the right side of the temperature frame 314d. The temperature alarm status area 328a specifies an upper alarm limit and a lower alarm limit. The upper alarm limit and the lower alarm limit define a temperature alarm range. An alarm associated with the patient's temperature is active when the patient's temperature level is outside the temperature alarm range.

In some embodiments, the PMP device 200 can measure the patient's temperature in either a predictive mode or in a direct mode. When the PMP device 200 measures the patient's temperature in the predictive mode, the PMP device 200 predicts the patient's current temperature based on periodic readings of the patient's temperature. When the PMP device 200 measures the patient's temperature in the direct mode, the PMP device 200 continually measures the patient's temperature.

The temperature value in the temperature frame 314d is based on measurements received from a thermometer attached to a patient. When the PMP device 200 measures the patient's temperature in the predictive mode, the thermometer can be located at various places on the patient's body. Example locations on the patient's body where the thermometer can be located include in the patient's mouth, on the patient's thigh, in the patient's armpit, in the patient's rectum, and other locations.

The display screen 218 enables a user to select the parameter reporting frames 314a-314d in order to change how the physiological parameters are represented in the parameter reporting frames 314a-314d. In other words, each of the parameter reporting frames 314a-314d contains an initial representation of a physiological parameter. The parameter reporting frame displays an alternate representation of the physiological parameter instead of the initial representation of the physiological parameter when a user selects the parameter reporting frame. For example, selecting the temperature frame 314d toggles the temperature value between being expressed in Fahrenheit or Centigrade. This feature is referred to as "tap to toggle." In another example, when a user selects the pulse rate frame 314b, the PMP device 200 displays a waveform in the pulse rate frame 314b instead of a number representing the patient's current pulse rate. The waveform represents a patient's pulse over time. In this example, when the user selects the pulse rate frame 314b again, the PMP device 200 displays a number in the pulse rate frame 314b representing the patient's current pulse rate. In yet another example, when the user selects the SpO2 frame 314c, the PMP device 200 displays a plethysmographic waveform view in the SpO2 frame 314c.

Furthermore, in the example of FIG. 3, the patient attribute area 316 contains a patient type that is labeled with the text "Adult." The patient type is located towards the center of the patient attribute area 316. Patient-related attribute values that are labeled with the text ("HEIGHT"), ("WEIGHT"), ("PAIN") and ("RR") are located to the right side of the patient type button 316b. A save button 316g that is labeled with the text ("Save") is located at the right side of the patient attribute area 316.

Figure 4:
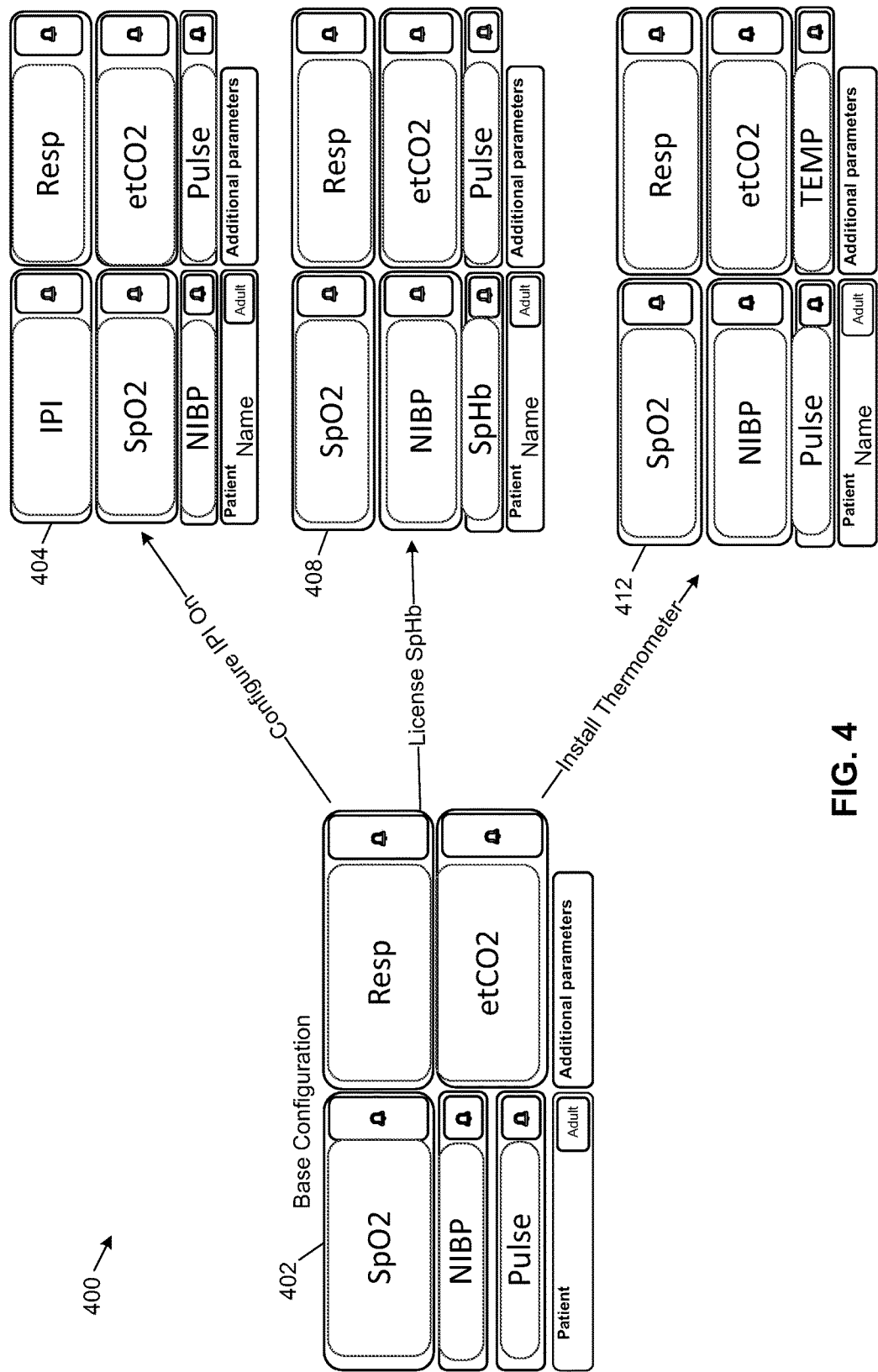
FIGS. 4-6 illustrate example user interface presentations for the physiological parameter monitoring platform device of FIG. 2A.
Figure 5:
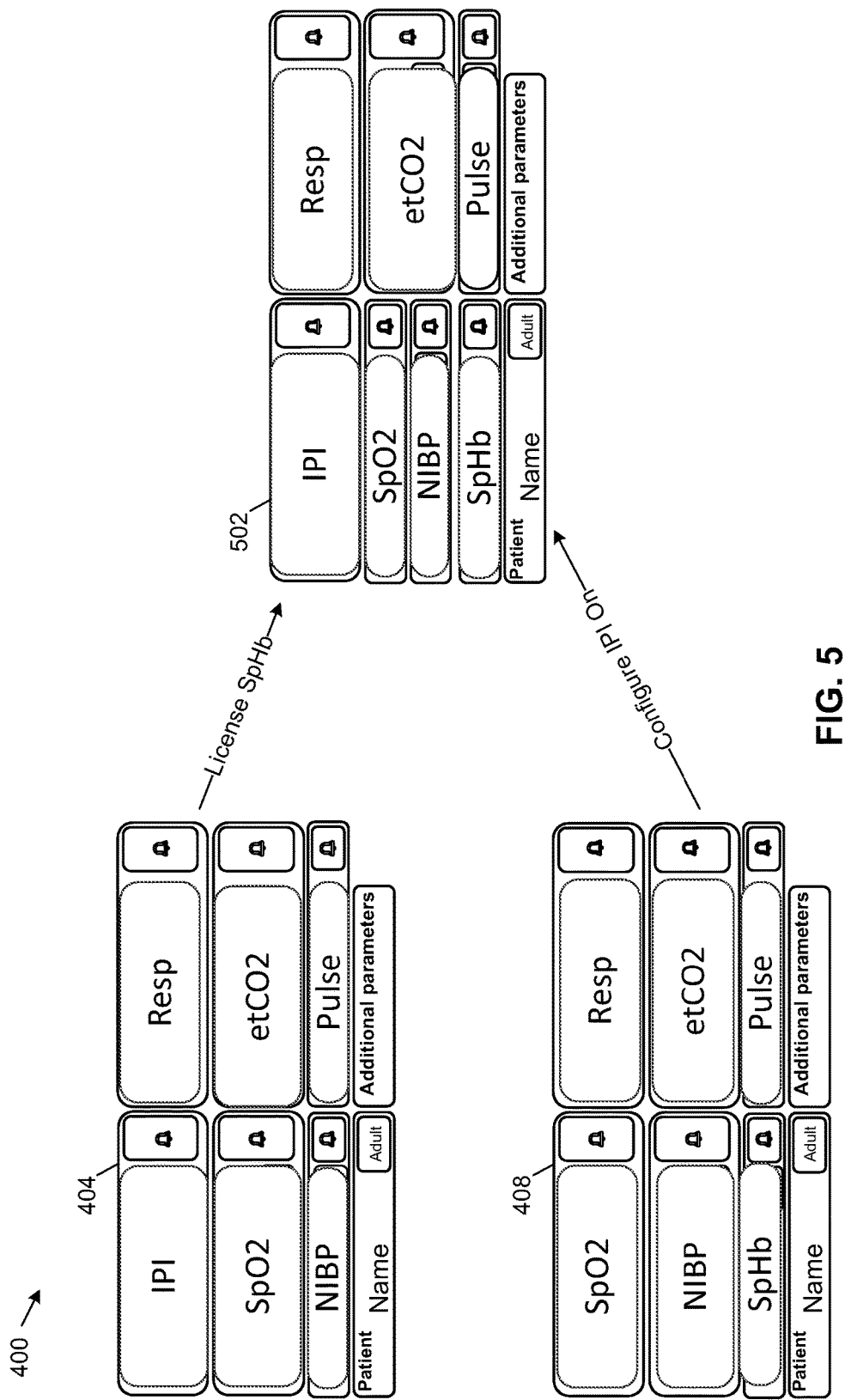
Figure 6:
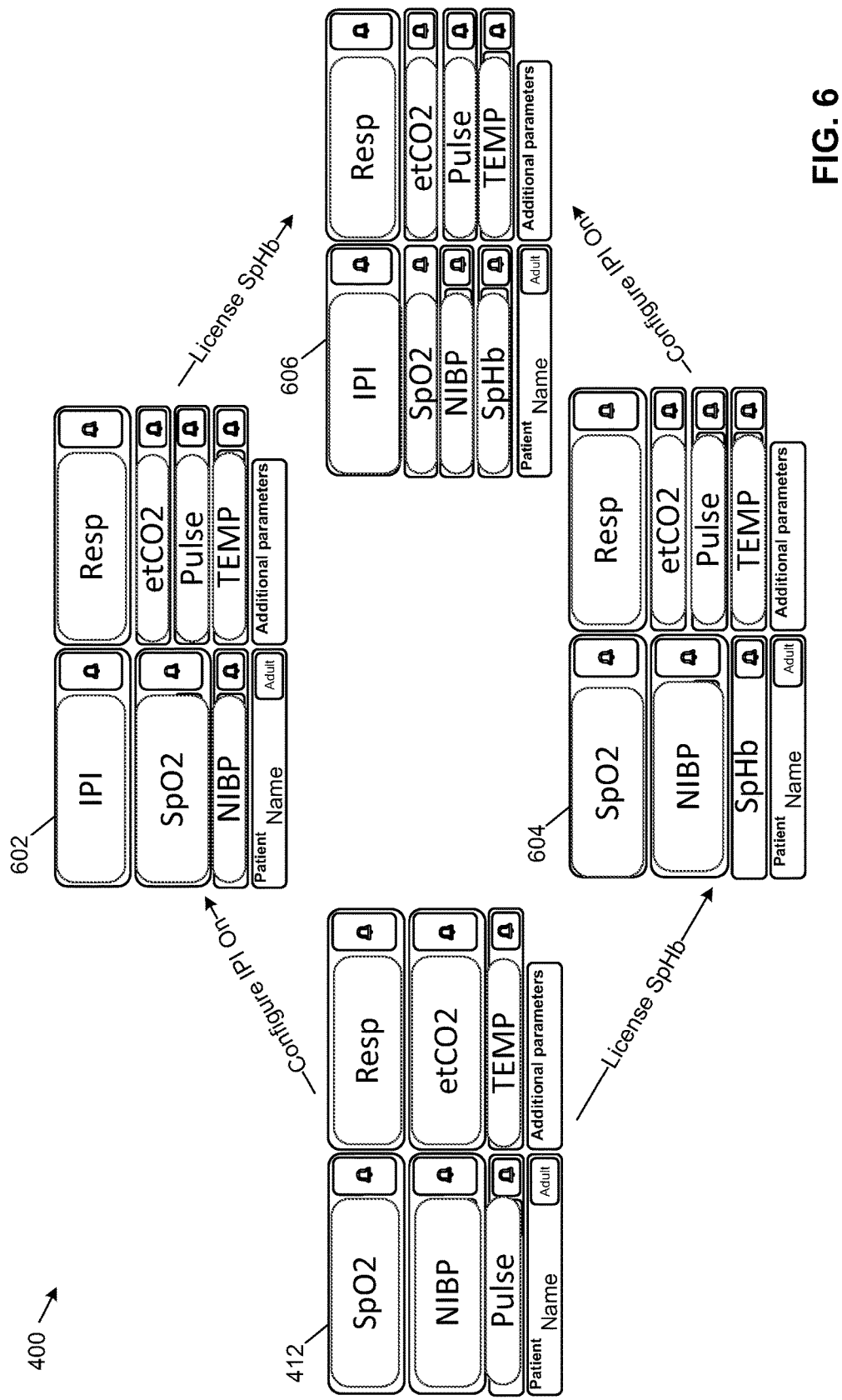

FIGS. 4, 5 and 6 illustrate example user interface presentations for the PMP device 200 based on physiological hardware modules installed in the PMP device 200. Different installed physiological modules result in different user interface presentations. In this disclosure, when a physiological hardware module is installed in the PMP device 200, it is also considered to be connected in the PMP device 200. In examples, some physiological modules may not be installed, but may be temporarily connected wirelessly. In other examples, the modules may be logical modules, rather than physical modules.

For example, FIG. 4 shows an example system 400 including a base configuration 402 that includes display areas for SPO2 (oxygen saturation), NIBP (non-invasive blood pressure), RR (respiration rate), Pulse (pulse rate) and etCO2 (end-tidal carbon dioxide). For the example base configuration 402, the PMP device 200 is configured with an oxygen saturation sensor module, an NIBP module, a respiration rate sensor module, a pulse rate sensor module and an end-tidal carbon dioxide sensor module and these modules are installed on the PMP device 200.

When the PMP device 200 is configured with the oxygen saturation sensor module, non-invasive blood pressure module, respiration rate sensor module, pulse rate sensor module and end-tidal carbon dioxide sensor module and these modules are installed in the PMP device 200, space is allocated on the user interface of PMP device 200 to display physiological parameters from these modules. For example, areas are allocated on the user interface of PMP device 200 for the display of oxygen saturation, non-invasive blood pressure, respiration rate, pulse rate and end-tidal carbon dioxide. In a similar manner, when a physiological module is uninstalled at the PMP device 200, the PMP device 200 is reconfigured to remove or reassign an area of space previously allocated on the user interface of the PMP device 200 for the physiological module that is uninstalled.

In examples, the user interface for PMP device 200 displays the base configuration 402 regardless of whether sensor devices corresponding to the physiological modules are connected to a patient. For example, the user interface for PMP device 200 displays an area for ETCO2 when an ETCO2 module is installed in PMP device 200, regardless of whether an ETCO2 sensor is actually connected to the patient and obtaining physiological data from the patient.

When a configuration of PMP device 200 changes as a results of installing one or more additional HCE modules in PMP device 200 or as a result of activating one or more operational features of PMP device 200, the base configuration 402 changes. For example, when an integrated pulmonary index (IPI) is configured on for the PMP device 200, base configuration 402 changes to example configuration 404. In example configuration 404, a user interface display area is added for IPI and display areas SpO2 and Pulse become smaller. The IPI provides a measurement of a patient's pulmonary health or breathing, typically as a number from 1 to 10.

When a device for calculating noninvasive total hemoglobin (SpHb) is installed at PMP device 200, base configuration 402 changes to example configuration 408. When a thermometer module is installed in PMP device 200, base configuration 402 changes to example configuration 412.

In addition to HCE modules being installed and operational features being activated at base configuration 402, HCE modules may be installed and operational features may be activated for other configuration. FIG. 5 shows how configurations 404 and 408 may change when additional HCE modules are installed or operational features are activated in system 400. For example, when a SpHb module is added to configuration 404, configuration 404 changes to example configuration 502. Similarly, when IPI is configured for configuration 408, configuration 408 changes to the same configuration 502.

FIG. 6 shows how configuration 412 may change when additional HCE modules are installed or operational features are activated. For example, when IPI is configured on at PMP device 200 having a configuration 412, configuration 412 changes to example configuration 602. When a SpHb module is added to configuration 412, configuration 412 changes to example configuration 604.

When a SpHb module is added to configuration 602, configuration 602 changes to example configuration 606. When IPI is configured on at PMP device 200 having a configuration 604, configuration 604 similarly changes to configuration 616.

For the examples shown in FIGS. 4, 5 and 6, the added HCE modules are typically installed and configured and operational features are typically activated and configured during manufacture before the PMP device 200 is used in a medical setting. When the PMP device 200 is used, the user interface of the PMP device 200 provides display areas for the features and sensor devices as described above and as shown in FIGS. 4, 5 and 6. In examples, the placement of a display of physiological parameters on the user interface of PMP device 200 may vary from the examples shown in FIGS. 4, 5 and 6.

In other examples, the user interface of PMP device 200 may be dynamically configured based on the detection of one or more physiological sensor devices or based on the activation of one or more operational features. For example, if a wireless thermometer device is detected at PMP device 200 having base configuration 402, in examples base configuration 402 changes to configuration 412.

Figure 7A:
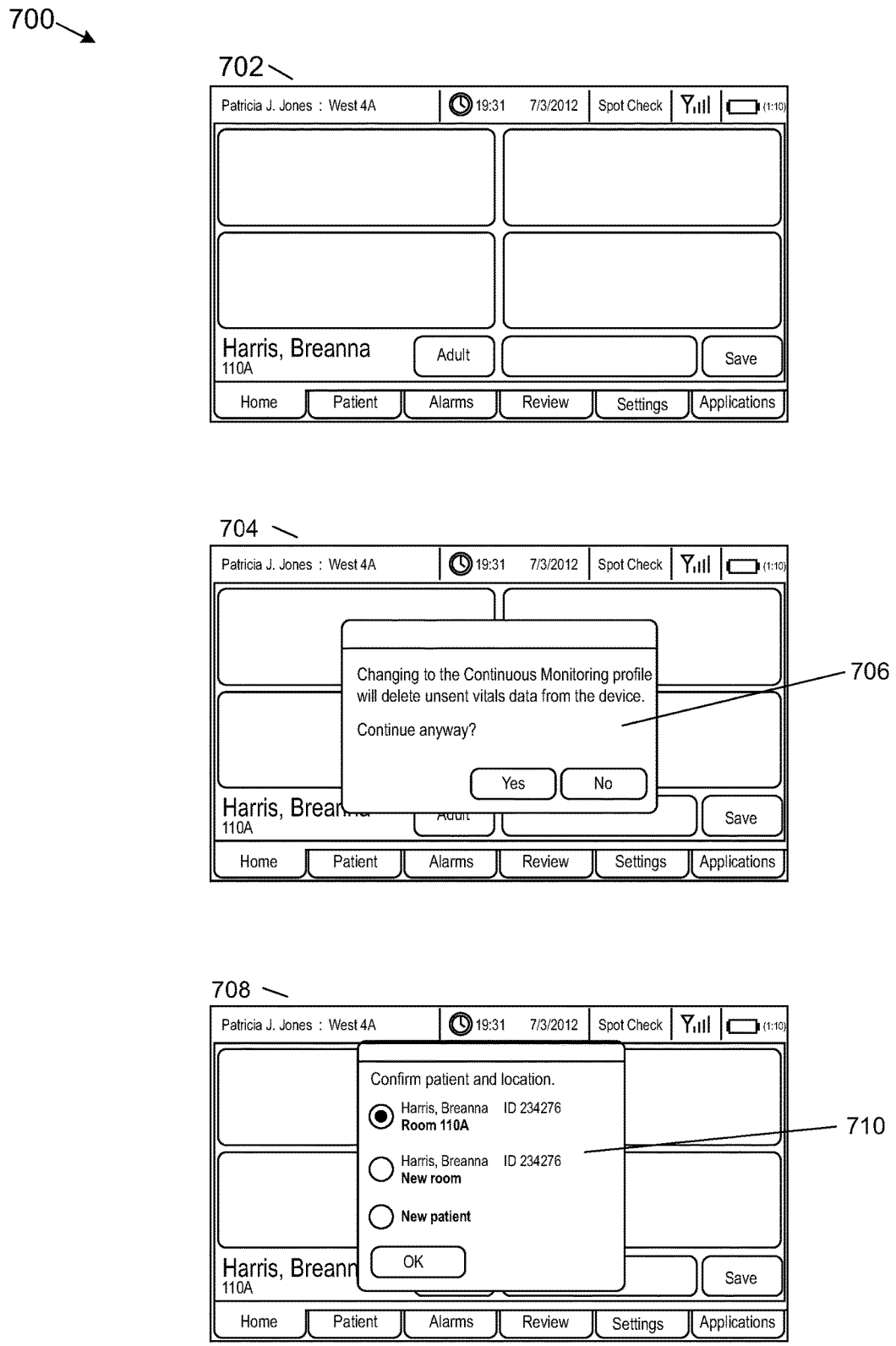
FIGS. 7A-7B illustrate example display screens for automatically changing a workflow for a patient.
Figure 7B:
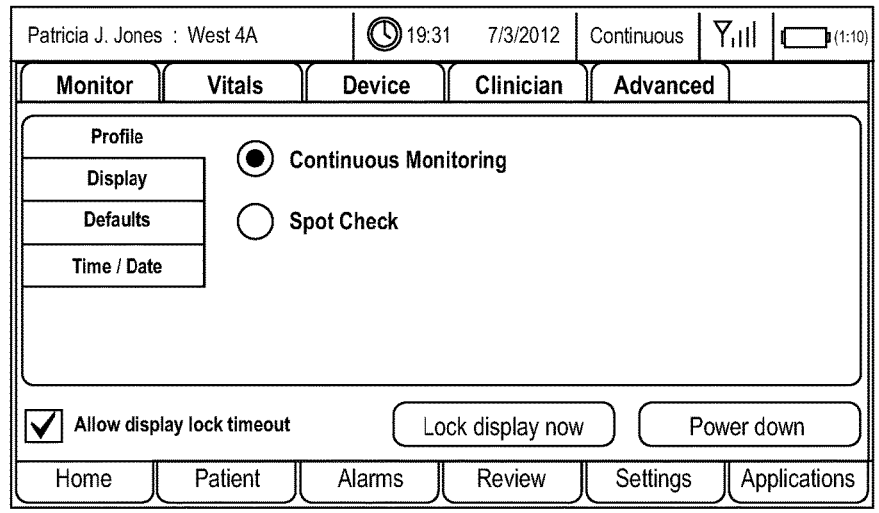
Figure 7B:
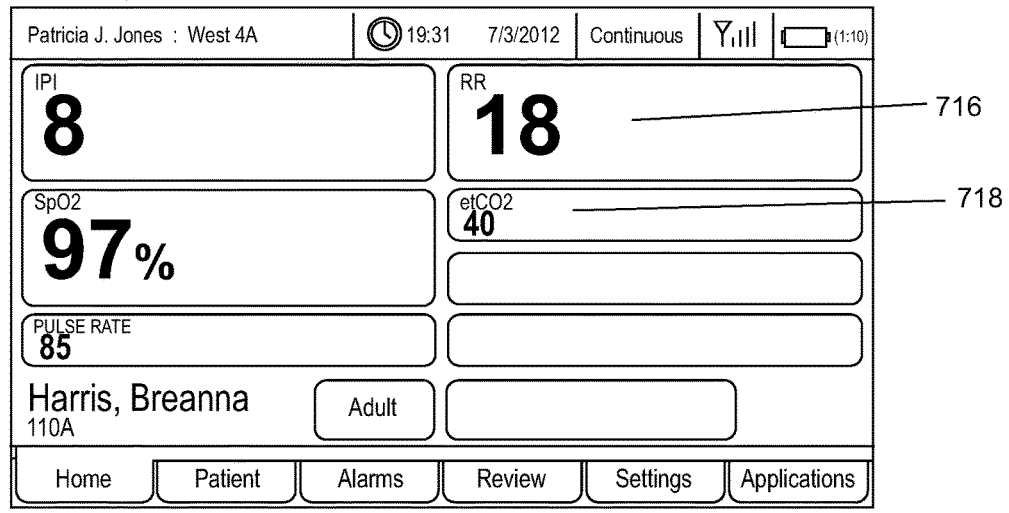

FIGS. 7A-7B show example display screens 700 for automatically changing a workflow for a patient. In these examples, the PMP device 200 is configured to automatically sense a change in the way the device is being used. Based on this change in use, the PMP device 200 can change workflows to adjust.

For example, the PMP device 200 may be operating in a spot check workflow for a patient. In the spot check workflow, for example, clinicians may obtain vital signs for the patient, for example NIBP and temperature, on a non-continuous basis, for example one or more times during a nurse's shift.

FIG. 7A shows an example home screen 702 of a patient for the PMP device 200 when the PMP device 200 is in the spot check workflow. For the example home screen 702, no sensors are connected to the patient so physiological data for the patient is not being displayed on the home screen 702.

If a clinician connects a continuous monitoring sensor device, for example an ETCO2 sensor device to the patient, the workflow for the patient becomes a continuous workflow. When the PMP device 200 is operating with the continuous workflow, the PMP device 200 obtains a series of measurements of one or more physiological parameters of a single monitored patient continuously over a period of time. The continuous measurements can be taken over short intervals, such as 1 millisecond, 0.5 second, 1 second, 2 seconds, etc.

In examples, a display screen 704 may be displayed on the PMP device 200 to alert the clinician that the PMP device 200 is changing to a continuous workflow. In example display screen 704, the clinician is alerted to the change in workflow by a dialog box 706 and asked to confirm or reject the change.

When the clinician approves the change to the continuous workflow, the PMP device 200 displays example display screen 708, asking the clinician to verify the identity of the patient. In example display screen 708, the clinician is asked to confirm or reject the change via dialog box 710.

When the clinician verifies the identity of the patient, example display screen 712 is displayed on the PMP device 200. The example display screen 712 shows that the workflow has been changed to continuous monitoring for the patient on PMP device 200. Other and different display screens may be displayed.

Example display screen 714 shows that the PMP device 200 is now in continuous monitoring mode. Physiological data being monitored in continuous monitoring include respiration rate (RR) 716 and end-tidal carbon dioxide (ETCO2) 718.

In examples, when a physiological sensor device for continuous monitoring is removed from a patient, the workflow for the patient may be automatically changed on PMP device 200 from continuous monitoring to spot check monitoring. Automatically changing a workflow from a spot workflow to a continuous workflow may be referred to as auto up-shift. Similarly, changing a workflow from a continuous workflow to a spot workflow may be referred to as auto down-shift.

The automatic shifting of the workflows based on the current status of the PMP device allows for greater usability. Such transitions allow the user to easily configure the device as desired to show the relevant physiological data that is being collected. In an alternative embodiment, the PMP device can be configured to automatically change workflow configurations (i.e., auto up-shift or down-shift) without prompting for confirmation from the user. In such a scenario, for example, the PMP device can automatically transition from a spot check workflow to a continuous workflow when a continuous sensor device is paired to the PMP device.

FIG. 8 shows an illustration of an example review zoom feature 800 of the user interface of the PMP device 200. The review zoom feature permits the user interface to automatically zoom in on a section of a trend display of physiological data and display physiological data at a relevant time interval, such as one-minute intervals, on the user interface. The illustration of the review zoom feature 800 includes example trend displays 802 and 804. Trend display 802 shows a display of physiological data for selected physiological parameters at one hour time intervals. For example, physiological data for example physiological parameters IPI, ETCO2, RR and SPO2 are displayed at hourly intervals from 6:00 to 14:00. Physiological data at time periods within each hour time interval are not shown on trend display 802.

When an alarm occurs, an exception event is generated and a new column, for example column 806, is displayed corresponding to when the alarm occurred. For example, if the alarm occurred at 8:11, the new column, shown having column header 8:11+, is displayed between the 8:00 and 9:00.

When the column header of column 806 is selected, trend display 804 is displayed. Trend display 804 shows physiological data for the selected parameters at minute intervals instead of the hour intervals shown in trend display 802. In addition, as shown in FIG. 8, a column corresponding to the minute selected in trend display 802 is shown directly underneath the selected minute in trend display 804. For example, column 808, corresponding to time 8:11 is shown directly under column 806. In this manner, the selected time is centered in trend display 804 around the minutes in which the alarm occurred, providing quick access to the selected physiological data and avoiding the need to search for the selected minute in trend display 804.

In examples, when a user wants to return to the normal display of one hour intervals, the user clicks an area of the header in trend display 804 and trend display 802 is displayed again. In examples, the time intervals or one hour for trend display 802 and 1 minute for trend display 804 can be adjusted to other time interval values.

Figure 9:
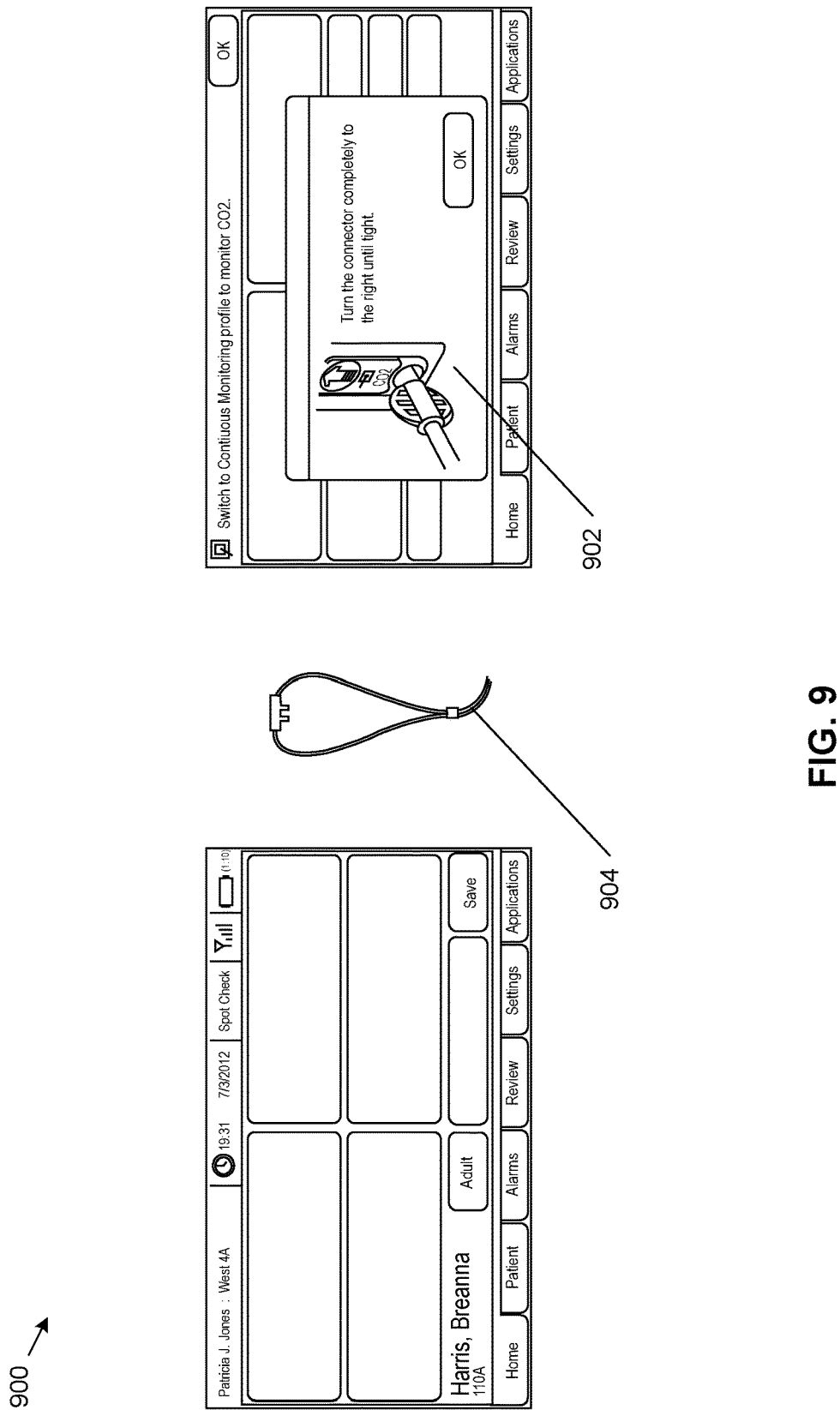
FIG. 9 illustrates example screen shots when a CO2 sensor is incorrectly connected to the physiological parameter monitoring platform device of FIG. 2A.

FIG. 9 shows screen shots of example displays 900 on the user interface of the PMP device 200 when a CO2 sensor is connected to the PMP device 200. When a CO2 sensor 904, for example a physiological sensor that monitors end-tidal carbon dioxide, is connected to a patient, the CO2 sensor must be correctly attached in order to obtain accurate readings from the CO2 sensor. However it is possible, to connect the CO2 sensor incorrectly, thereby producing inaccurate readings from the CO2 sensor. Furthermore a clinician may not realize that the CO2 sensor is connected incorrectly.

A common way of incorrectly connecting the CO2 sensor is to fail to completely tighten a connection of the CO2 sensor to the PMP device 200. To mitigate against incorrectly tightening the connection of the CO2 sensor to the PMP device 200, the clinician is prompted each time the CO2 sensor is attached to the PMP device 200 to remind the clinician to connect the CO2 sensor correctly.

As shown, in FIG. 9, whenever a CO2 sensor is attached to PMP device 200, an example window 902 is displayed on the user interface of the PMP device 200. For example, the window 902 includes a message indicating that a connector on the CO2 sensor must be turned completely to the right until tight. The window 902 and the message alert the clinician that the CO2 sensor must be properly installed for accurate measurements to be taken. Other windows and messages are possible.

Figure 10:
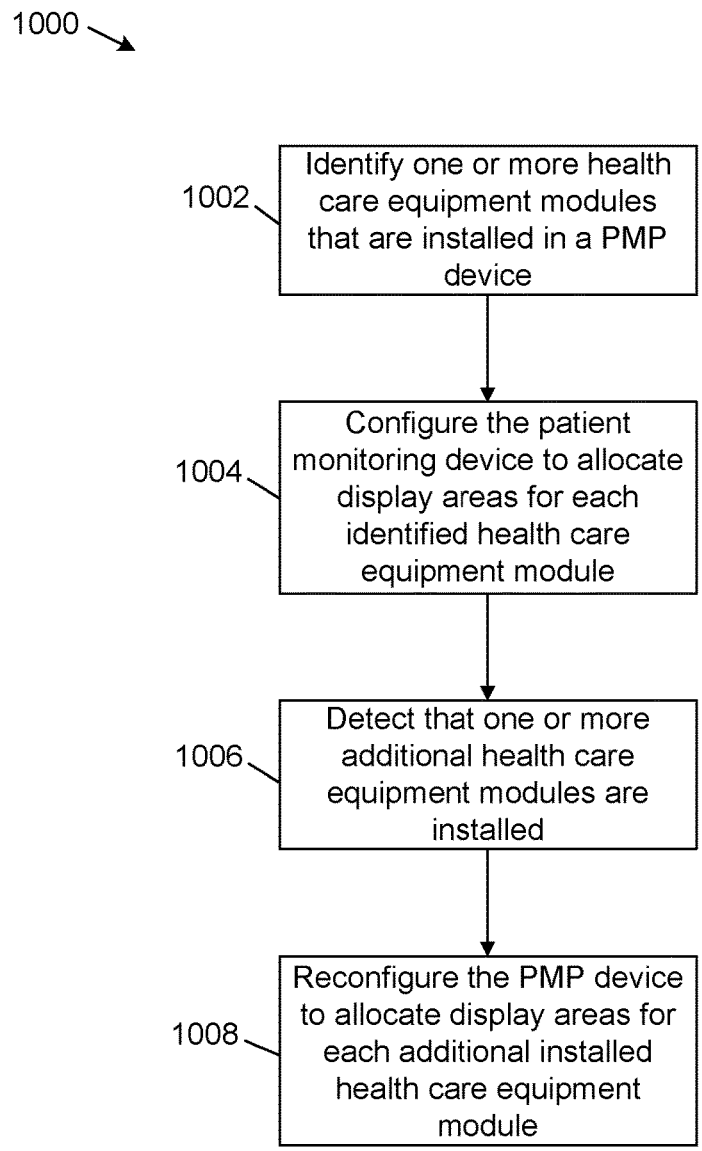
FIG. 10 illustrates an example flowchart for a method for configuring a display of area of the user interface for the physiological parameter monitoring platform device of FIG. 2A.

FIG. 10 shows an example flowchart for a method 1000 for configuring a display of physiological data for a patient. At operation 1002, one or more health care equipment (HCE) modules that are installed in a physiological parameter monitoring platform device, for example PMP device 200, are identified. The one or more HCE modules are used to process physiological data obtained by a corresponding physiological sensor that is typically connected to or attached to a patient. Examples of HCE modules include the non-invasive blood pressure (NIBP) module 216, the temperature measurement module 212 and the SpO2 module 214. Other HCE modules are possible.

At operation 1004, the physiological parameter monitoring platform device is configured to allocate display areas for each of the identified HCE modules. The display areas provide for a display of physiological data obtained by the HCE modules. The display areas are located on a display screen of the physiological parameter monitoring platform device. The display areas are specific to the HCE modules configured, as shown in FIGS. 4-6.

At operation 1006, the physiological parameter monitoring platform device detects that one or more additional HCE modules are installed in the physiological parameter monitoring platform device. At operation 1008, the physiological parameter monitoring platform device is reconfigured to allocate display space for each of the additional HCE modules. In the process of allocating display space for each of the additional HCE modules, display space for previously identified HCE modules may be decreased in size, as shown in FIG. 4-6. For example, when a NIBP module is added to base configuration 402, resulting in configuration 410, display space for pulse rate in configuration 410 is smaller than display space for pulse rate in base configuration 402.

Figure 11:
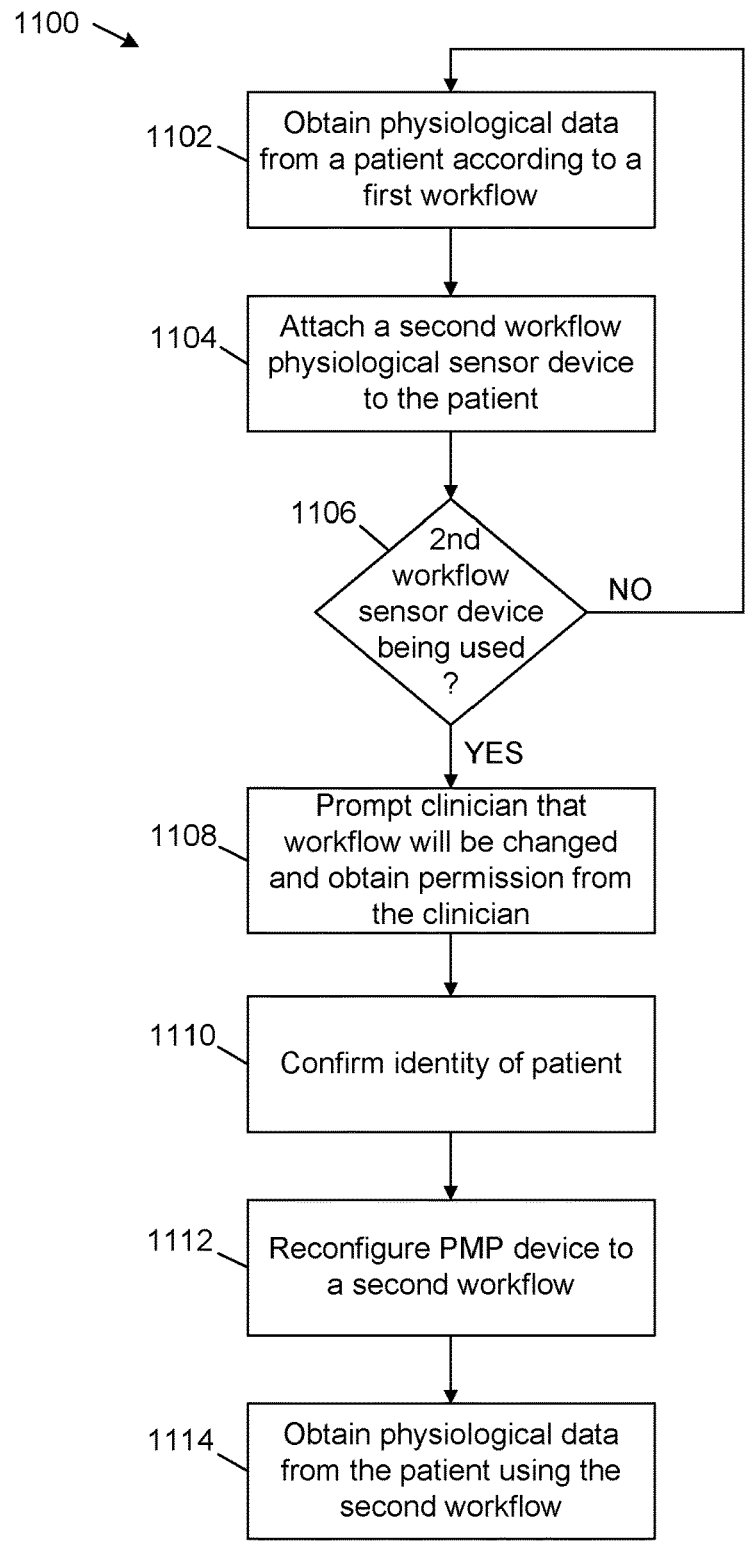
FIG. 11 illustrates an example flowchart for a method for changing a workflow based on the detection of a physiological sensor device.

FIG. 11 shows an example flowchart for a method 1100 for changing a workflow based on the detection of a physiological sensor device. At operation 1102, physiological data is obtained from a patient according to a first workflow. For example, oxygen saturation may be measuring using a spot workflow, for example by a nurse attaching an SPO2 sensor to a finger of the patient and taking a measurement during the nurse's shift.

At operation 1104, a second workflow physiological sensor device is attached to the patient. For example, a clinician may have attached a sensor device for measuring end-tidal carbon dioxide (ETCO2) to the patient. ETCO2 is typically measured continuously as part of a continuous workflow.

At operation 1106, a determination is made as to whether a second workflow physiological sensor device is attached to the patient. When it is determined at operation 1106 that the second workflow physiological sensor device is attached to the patient, at operation 1108, the clinician is prompted that that the workflow is being changed from the first workflow to the second workflow, for example from the spot check workflow to the continuous workflow. The clinician is also prompted to provide permission for permitting the workflow to be changed from the first workflow to the second workflow. Prompting is done to alert the clinician that the physiological parameter monitoring platform device is ready to change the workflow and to indicate to the clinician, in examples, that other changes may occur. For example, vital signs data obtained using the spot workflow and not yet sent to the EMR system may be deleted from the physiological parameter monitoring platform device.

At operation 1110, after the clinician gives permission for the change of workflow, the clinician is prompted to confirm the identity of the patient. In examples, a dialog box similar to dialog box 705, may be displayed showing identification information for the patient and asking the clinician to confirm.

At operation 1112, after the clinician confirms the identity of the patient, the physiological parameter monitoring platform device is reconfigured to the second workflow, for example PMP device 200 is reconfigured to the continuous workflow. At operation 1114, physiological data is obtained from the patient using the second workflow.

Figure 12:
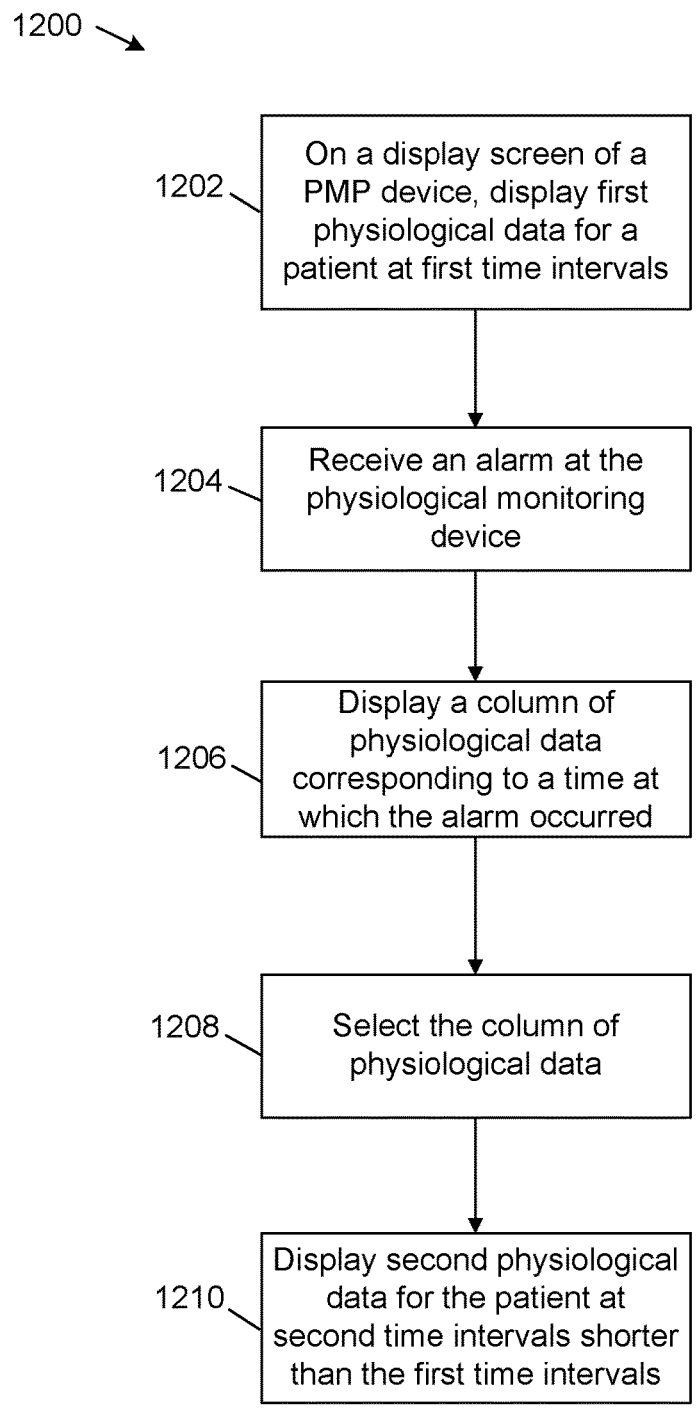
FIG. 12 illustrates an example flowchart for a method for implementing a review zoom function of the user interface of the physiological parameter monitoring platform device device of FIG. 2A.

FIG. 12 shows an example flowchart for a method 1200 for implementing a review zoom function of the user interface of the physiological parameter monitoring platform device. The review zoom function permits a clinician to automatically zoom into physiological data from a patient when an alarm condition occurs.

At operation 1202, physiological data for a patient is displayed at first time intervals on a display screen of the physiological parameter monitoring platform device. In examples, the physiological data is obtained at different times, typically at one hour intervals, and the display of the physiological data at each of these times provides a display of a trend in the physiological data over time.

At operation 1204, an alarm is received at the physiological parameter monitoring platform device. The alarm typically indicates that one or more physiological parameters being monitored for the patient have values outside an allowable range for these physiological parameters. For example, a physiological parameter by be lower than a lower threshold limit or higher than an upper threshold limit.

At operation 1206, a column of physiological data is displayed corresponding to a time at which the alarm occurred. For example, if the alarm occurred at 8:11, a column of physiological data at time 8:11 is displayed. The column of physiological data is placed between hourly columns of physiological data, for example between 8:00 and 9:00, as shown in FIG. 8.

At operation 1208, the column of physiological data is selected, typically by clicking on a header of the column. For example, the column may be selected by clicking on the column header of column 806. As shown in FIG. 8 the header of column 806 is indicated as 8:11+.

As a result of selecting the header of the column displaying the alarm data, at operation 1210, physiological data is displayed at shorter time intervals than previously displayed. For example, whereas at operation 1202, physiological data for the patient may be displayed at one hour intervals, at operation 1210, physiological data for the patient may be displayed at one minute time intervals.

In addition, as shown in column 808 of FIG. 8, the physiological data at the one minute time intervals is positioned under the corresponding time at which the alarm occurred. For example, column 808 is displayed directly under column 806. This permits the clinician to easily view physiological data at minutes intervals around the time at which the alarm occurred, and minimizes any scrolling the clinician may need to do in order to locate alarm data.

Figure 13:
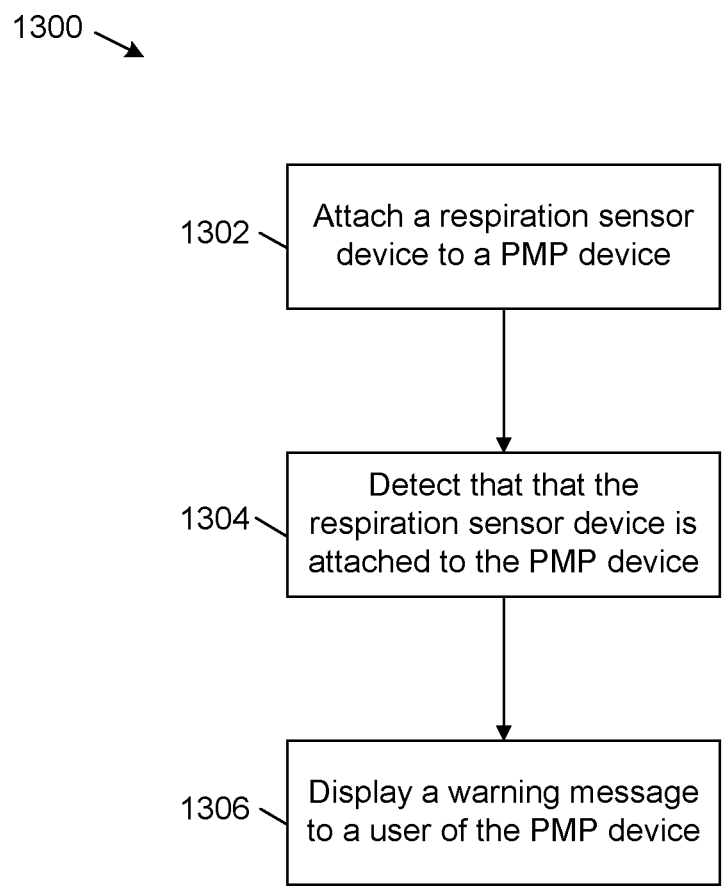
FIG. 13 illustrates an example flowchart for a method for providing an alert when a physiological sensor that measures respiration is incorrectly connected to the physiological parameter monitoring platform device of FIG. 2A.

FIG. 13 shows an example flowchart for a method 1300 for alerting a clinician when a physiological sensor that measures respiration is attached to a PMP device. An example of a physiological sensor that measure respiration is a physiological sensor that measures end-tidal carbon dioxide (ETCO2).

At operation 1302, a respiration sensor device is attached to PMP device 200. At operation 1304, the PMP device 200 detects that the respiration sensor is attached to the PMP device 200. In examples, the respiration sensor device includes a hose and the PMP device 200 includes a hose sensor. When the respiration sensor device is attached to the PMP device 200, the hose sensor detects that that the respiration sensor device is attached to the PMP device 200. It examples, the respiration sensor device triggers the hose sensor when the respiration sensor device is attached to the PMP device 200.

At operation 1306, a warning message is displayed on the physiological parameter monitoring platform device. An example warning message, shown on example window 902, instructs the clinician to turn a connector completely to the right until tight. Other warning messages are possible.

Figure 14:
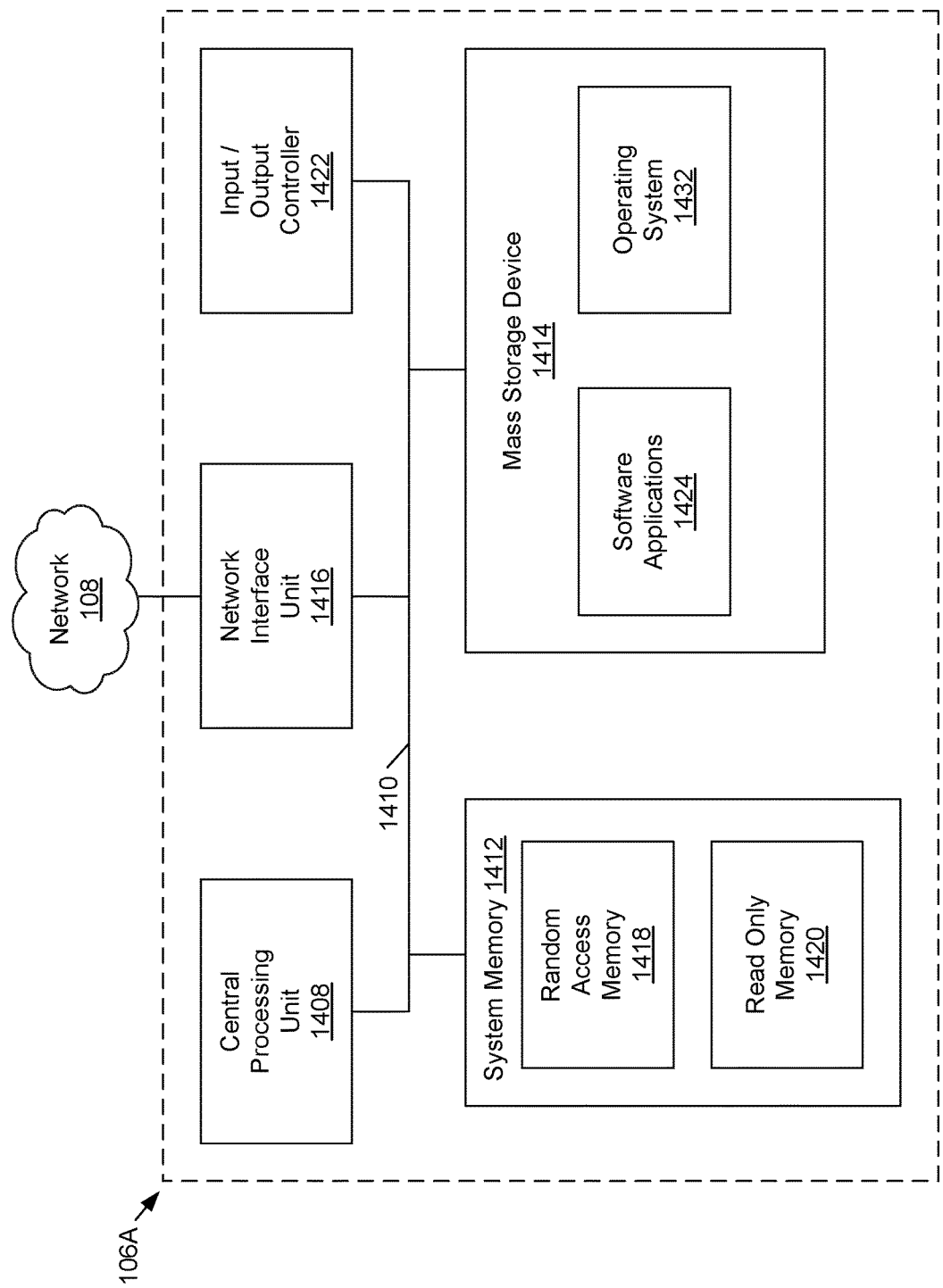
FIG. 14 illustrates example physical components of the physiological parameter monitoring platform device.

FIG. 14 illustrates example physical components of the PMP device 200. As illustrated in the example of FIG. 14, the PMP device 200 include at least one central processing unit ("CPU") 1408, a system memory 1412, and a system bus 1410 that couples the system memory 1412 to the CPU 1408. The system memory 1412 includes a random access memory ("RAM") 1418 and a read-only memory ("ROM") 1420. A basic input/output system containing the basic routines that help to transfer information between elements within the PMP device 200, such as during startup, is stored in the ROM 1420. The PMP device 200 further includes a mass storage device 1414. The mass storage device 1414 is able to store software instructions and data.

The mass storage device 1414 is connected to the CPU 1408 through a mass storage controller (not shown) connected to the bus 1410. The mass storage device 1414 and its associated computer-readable data storage media provide non-volatile, non-transitory storage for the PMP device 200. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the PMP device 200 can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the PMP device 200.

According to various embodiments of the invention, the PMP device 200 may operate in a networked environment using logical connections to remote network devices through the network 108, such as a local network, the Internet, or another type of network. The PMP device 200 connects to the network 108 through a network interface unit 1416 connected to the bus 1410. It should be appreciated that the network interface unit 1416 may also be utilized to connect to other types of networks and remote computing systems. The PMP device 200 also includes an input/output controller 1422 for receiving and processing input from a number of other devices, including a keyboard, a mouse, a touch user interface display screen, or another type of input device. Similarly, the input/output controller 1422 may provide output to a touch user interface display screen, a printer, or other type of output device.

As mentioned briefly above, the mass storage device 1414 and the RAM 1418 of the PMP device 200 can store software instructions and data. The software instructions include an operating system 1432 suitable for controlling the operation of the PMP device 200. The mass storage device 1414 and/or the RAM 1418 also store software instructions, that when executed by the CPU 1708, cause the PMP device 200 to provide the functionality of the PMP device 200 discussed in this document. For example, the mass storage device 1414 and/or the RAM 1418 can store software instructions that, when executed by the CPU 1708, cause the PMP device 200 to display screen 218 and other screens.

It should be appreciated that various embodiments can be implemented (1) as a sequence of computer implemented acts or program modules running on a computing system and/or (2) as interconnected machine logic circuits or circuit modules within the computing system. The implementation is a matter of choice dependent on the performance requirements of the computing system implementing the invention. Accordingly, logical operations including related algorithms can be referred to variously as operations, structural devices, acts or modules. It will be recognized by one skilled in the art that these operations, structural devices, acts and modules may be implemented in software, firmware, special purpose digital logic, and any combination thereof without deviating from the spirit and scope of the present invention as recited within the claims set forth herein.

Although the invention has been described in connection with various embodiments, those of ordinary skill in the art will understand that many modifications may be made thereto within the scope of the claims that follow. For example, it should be appreciated that the screens illustrated in this document are merely examples and that in other embodiments equivalent screens can have different contents and appearances. Accordingly, it is not intended that the scope of the invention in any way be limited by the above description, but instead be determined entirely by reference to the claims that follow.

What is claimed is:

1. A method for displaying patient physiological data on a physiological parameter monitoring device, the method comprising:
    identifying one or more physiological sensor modules that are connected in a physiological parameter monitoring device;
    after identifying the one or more physiological sensor modules, configuring the physiological parameter monitoring device so that one or more display areas are allocated on a display screen of the physiological parameter monitoring device for displaying physiological data for the patient, at least one separate display area being allocated for each identified physiological sensor module;
    detecting that one or more additional physiological sensor modules are connected in the physiological parameter monitoring device;
    after the one or more additional physiological sensor modules are detected as being connected, automatically configuring the physiological parameter monitoring device to include one or more additional display areas on the display screen for displaying physiological data for the patient, at least one separate additional display area being allocated for each of the additional physiological sensor modules that is connected, wherein a size of the at least one separate display area is decreased to provide space for the at least one separate additional display area;
    uninstalling a physiological sensor module from the physiological parameter monitoring device;
    as a result of uninstalling the physiological sensor module, reconfiguring the physiological parameter monitoring device to remove a display screen area corresponding to the physiological sensor module;
    receiving selection of a zoom feature button;
    displaying a trend display of selected physiological data at a periodic time interval, the trend display including numerical values of recorded measurements of the selected physiological data in tabular format; and
    inserting a new column into the trend display at a time at which an alarm occurred.

2. The method of claim 1 wherein the one or more physiological sensor modules are connected during manufacture of the physiological parameter monitoring device.

3. The method of claim 1, wherein the one or more physiological sensor modules are hard-wired physiological sensor devices.

4. The method of claim 1, wherein the one or more physiological sensor devices are wireless devices.

5. The method of claim 1, wherein reconfiguring the physiological parameter monitoring device further comprises adjusting a display area size corresponding to one or more other physiological sensor modules.

6. The method of claim 1, further comprising:
    activating a feature of the physiological parameter monitoring device relating to monitoring physiological data from the patient; and
    as a result of activating the feature, configuring the physiological parameter monitoring device to include a display area on the display screen associated with the feature.

7. The method of claim 6, wherein the feature is related to a measurement of a pulmonary health of the patient.

8. The method of claim 1, further comprising displaying a second trend display when a column of the trend display is selected, the second trend display having shorter periodic time interval.

* * * * *